United States Patent
Thompson et al.

(10) Patent No.: US 7,323,494 B2
(45) Date of Patent: Jan. 29, 2008

(54) COMPOUNDS AND METHODS

(75) Inventors: Scott K. Thompson, King of Prussia, PA (US); James S. Frazee, King of Prussia, PA (US); Lara S. Kallander, King of Prussia, PA (US); Chun Ma, Edgewater, NJ (US); Joseph Marino, King of Prussia, PA (US); Michael J. Neeb, King of Prussia, PA (US); Ajita Bhat, Andover, MA (US)

(73) Assignee: SmithKline Beecham Corporation, Philadelphia, PA (US)

(*) Notice: Subject to any disclaimer, the term of this patent is extended or adjusted under 35 U.S.C. 154(b) by 465 days.

(21) Appl. No.: 10/508,822

(22) PCT Filed: Mar. 26, 2003

(86) PCT No.: PCT/US03/09039

§ 371 (c)(1),
(2), (4) Date: Sep. 22, 2004

(87) PCT Pub. No.: WO03/082192

PCT Pub. Date: Oct. 9, 2003

(65) Prior Publication Data

US 2005/0165045 A1    Jul. 28, 2005

Related U.S. Application Data

(60) Provisional application No. 60/368,415, filed on Mar. 27, 2002.

(51) Int. Cl.
*A61K 31/343* (2006.01)
*C07D 307/81* (2006.01)

(52) U.S. Cl. .................. 514/469; 514/300; 514/301; 514/302; 514/303; 514/367; 514/375; 514/394; 514/415; 514/443; 546/113; 546/114; 546/115; 546/116; 546/118

(58) Field of Classification Search ............ 546/113, 546/114, 115, 116, 118; 548/152, 178, 179, 548/180, 217, 309.7, 504; 549/49, 58, 467; 514/300, 301, 302, 303, 367, 375, 394, 415, 514/443, 469
See application file for complete search history.

(56) References Cited

U.S. PATENT DOCUMENTS

| | | | |
|---|---|---|---|
| 2003/0153541 A1 | 8/2003 | Dudley et al. | 514/171 |
| 2003/0162758 A1 | 8/2003 | Schwartz et al. | 514/172 |
| 2003/0229062 A1 | 12/2003 | Schwartz et al. | 514/177 |
| 2004/0072868 A1 | 4/2004 | Collins et al. | 514/318 |
| 2004/0266663 A1 | 12/2004 | Schwartz et al. | 514/2 |
| 2005/0036992 A1 | 2/2005 | Saez et al. | 424/93.21 |
| 2005/0107444 A1 | 5/2005 | Thompson et al. | 514/345 |
| 2005/0113580 A1 | 5/2005 | Thompson et al. | 546/268.1 |
| 2005/0131014 A1 | 6/2005 | Cillini et al. | 514/311 |
| 2005/0171084 A1 | 8/2005 | Cairns et al. | 514/210.21 |
| 2005/0282750 A1 | 12/2005 | Schwartz et al. | 514/12 |
| 2005/0282908 A1 | 12/2005 | Collins et al. | 514/620 |

FOREIGN PATENT DOCUMENTS

| | | |
|---|---|---|
| EP | 0 394 440 | 10/1990 |
| WO | WO 00/54759 | 9/2000 |
| WO | WO 01/60818 | 8/2001 |
| WO | WO 02/24632 | 3/2002 |
| WO | WO 03/082205 | 10/2003 |
| WO | WO 03/082802 | 10/2003 |
| WO | WO 04/043939 | 5/2004 |
| WO | WO 04/058819 A2 | 7/2004 |
| WO | WO 04/110368 A2 | 12/2004 |
| WO | WO 04/110375 A2 | 12/2004 |
| WO | WO 05/009383 A2 | 2/2005 |
| WO | WO 05/013946 A2 | 2/2005 |
| WO | WO 05/055998 A1 | 6/2005 |
| WO | WO 06/000576 A2 | 1/2006 |
| WO | WO 06/000577 A2 | 1/2006 |
| WO | WO 06/004030 A1 | 1/2006 |

OTHER PUBLICATIONS

Kuehm-Caubere et al, J. Chem. Soc., Perkin Transactions1, p. 2857-2862 (1997).*
U.S. Appl. No. 60/499,659, filed Sep. 3, 2003, Hoang et al.
U.S. Appl. No. 60/500,295, filed Sep. 4, 2003, Hoang et al.
U.S. Appl. No. 60/499,779, filed Sep. 3, 2003, Kallander et al.
U.S. Appl. No. 60/500,296, filed Sep. 4, 2003, Kallander et al.

(Continued)

*Primary Examiner*—Bernard Dentz
(74) *Attorney, Agent, or Firm*—Kathryn L. Sieburth; Mary E. McCarthy; Charles M. Kinzig

(57) ABSTRACT

Disclosed is a compound of having the formula:

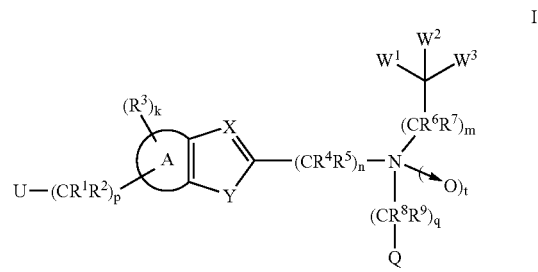

pharmaceutically acceptable salts or solvates thereof and pharmaceutical compositions containing the same, wherein the structural variables are as defined herein. The compounds, salts and solvates of this invention are useful as LXR agonists.

26 Claims, No Drawings

OTHER PUBLICATIONS

U.S. Appl. No. 60/499,762, filed Sep. 3, 2003, Hoang et al.
Database CAPLUS on STN (Colombus, OH, USA), No. 128:22779, "Efficient Selective Synthesis of 2-Substituted Indoles from Complex-Base-Promoted Arynic Cyclizations". Abstract, Kuehn-Caubere et al., Oct. 1997.
Grefhorst et al. *Am. J. Physiol. Endocrinol. Metab.*, 289: E829-E838 (2005).
Groot et a. *J. Lipid Res.*, 46: 2182-2191 (2005).
Jaye et al. *J. Med. Chem.*, 48: 5419-5422 (2005).
Ogawa et al. *Circ. Res.*, 96: e59-e67 (2005).
Quinet et al. *J. Lipid Res.*, 45: 1929-1942 (2004).
Miao et al. *J. Lipid Res.*, 45: 1410-1417 (2004).
Schmuth et al. *J. Invest. Dermatol.* 123: 41-48 (2004).
Farnegardh et al. *J. Bil. Chem.*, 278(40): 38821-38828 (2003).
Wang et al. *J. Molec. Graphics and Modelling*, 22: 173-181 (2003).
Fowler et al. *J. Invest. Dermatol.*, 120: 246-255 (2003).
Joseph et al. *PNAS USA*, 99(11): 7604-7609 (2002).
Fluhr et al. *J. Invest. Dermatol.*, 125: 1206-1214 (2005).
Naik et al. *Circulation*, 113: 90-97 (2006).
Kruit et al. *Gastroenterology*, 128: 147-156 (2005).
Lafitte et al. *PNAS USA*, 100(9): 5419-5424 (2003).
Castrillo et al. *J. Biol. Chem.*, 278(12): 10443-10449 (2003).
Lafitte et al. *Mol. & Cell. Biol.*, 23(6): 2182-2191 (2003).
Collins et al. *J. Med. Chem.*, 45: 1963-1966 (2002).
Terasaka et al. *FEBS Journal*, 272: 1546-1556 (2005).
Collins et al. *Abstracts of Papers, 230th ACS National Meeting, Washington, DC. Aug. 28-Sep. 1, 2005. MEDI-237. Publisher: American Chemical Society, Washington, DC*.
Rao et al. *Abstracts of Papers, 229th ACS National Meeting, San Diego, CA. Mar. 13-17, 2005. COMP-258. Publisher: American Chemical Society, Washington, DC*.
Jon L. Collins. *Abstracts of Papers, 225th ACS National Meeting, New Orleans, LA. Mar. 23-27, 2003. MEDI-152. Publisher: American Chemical Society, Washington, DC*.
Collins et al. *Abstracts of Papers, 223rd ACS National Meeting, Orlando, FL. Apr. 7-11, 2002. MEDI-123. Publisher: American Chemical Society, Washington, DC*.
Angelo Gavezzotti. Acc. Chem. Res., 27: 309-314 (1994).
Vippagunta et al. Advanced Drug Delivery Reviews, 48: 3-26 (2001).
Office Action: U.S. Appl. No. 10/508,849, filed Feb. 5, 2007.

* cited by examiner

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: Modified polyhistidine tag

<400> SEQUENCE: 1

Met Lys Lys Gly His His His His His His Gly
 1               5                   10

<210> SEQ ID NO 2
```

```
<211> LENGTH: 25
<212> TYPE: PRT
<213> ORGANISM: Artificial Sequence
<220> FEATURE:
<223> OTHER INFORMATION: Biotinylated peptide comprising amino acids
      675-699 of SRC-1

<400> SEQUENCE: 2

Cys Pro Ser Ser His Ser Ser Leu Thr Glu Arg His Lys Ile Leu His
1               5                   10                  15

Arg Leu Leu Gln Glu Gly Ser Pro Ser
            20                  25
```

COMPOUNDS AND METHODS

This application is a 371 of International Application No. PCT/US03/09039, filed 26 Mar. 2003, which claims the benefit of U.S. Provisional Application No. 60/368,415, filed 27 Mar. 2002.

FIELD OF THE INVENTION

The present invention relates to compounds useful as modulating agents for liver X receptors (LXR). Additionally, the present invention relates to pharmaceutical formulations comprising such compounds, and the therapeutic use of the same.

BACKGROUND OF THE INVENTION

LXR is a transcription factor. The orphan nuclear receptors, LXRα and LXRβ (collectively LXR) play a role in the maintenance of cholesterol balance. Peet et al., *Curr. Opin. Genet. Dev.* 8:571-575 (1998). In addition, LXR binds to the ATP Binding Cassette Transporter-1 (ABCA1) gene and increases expression of the gene to result in increased ABCA1 protein. ABCA1 is a membrane bound transport protein that is involved in the regulation of cholesterol efflux from extrahepatic cells onto nascent HDL particles. Mutations in the ABCA1 gene are responsible for genetic diseases that result in the complete absence or low levels of HDL cholesterol and a concomitant highly increased risk of cardiovascular disease. See Brooks-Wilson et al., *Nat. Genet.* 22:336-345 (1999); Bodzioch et al., *Nat. Genet.* 22: 347-351 (1999); and Rust et al., *Nat. Genet.* 22:352-355 (1999). ABCA1 knockout mice homozygous for the mutation in the ABCA1 gene have virtually no plasma HDL, whereas the heterozygotes produce 50% of the HDL of wild type animals. See, Orso et al., *Nat. Genet.* 24:192-196 (2000) and McNeish et al., *Proc. Natl. Acad. Sci. USA* 97:4245-4250 (2000). ABCA1 knockout mice also show increased cholesterol absorption. See, McNeish et al., *Proc. Natl. Acad. Sci. USA* 97:4245-4250 (2000). Increased expression of ABCA1 results in increased HDL cholesterol, decreased absorption of cholesterol, and increased removal of excess cholesterol from extrahepatic tissues, including macrophages. LXR agonists also upregulate macrophage expression of apolipoprotein E and ABCG1, both of which contribute to the efflux of cellular cholesterol. By stimulating macrophage cholesterol efflux through upregulation of ABCA1, ABCG1, and apoE expression, as well as increasing the expression of other target genes including cholesteryl ester transfer protein and lipoprotein lipase, LXR agonists influence plasma lipoproteins.

Accordingly, compounds which function as LXR modulating agents, and particularly as LXR agonists, would be useful in methods of increasing ABCA1, ABCG1, and apolipoprotein E expression, increasing cholesterol efflux from peripheral cells, and treating LXR mediated diseases and conditions such as cardiovascular disease and inflammation.

SUMMARY OF THE INVENTION

This invention is directed to a compound of Formula I:

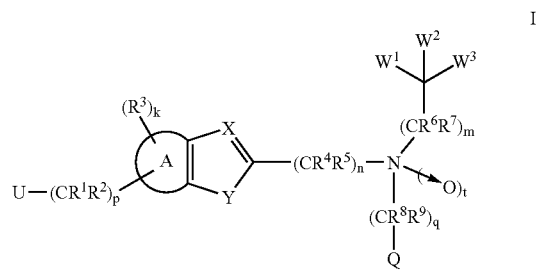

wherein:
X is CH or N;
Y is $N(R^{10})$, O, or S, wherein t is 0 or 1 when Y is $N(R^{10})$ or O, and t is 0 when Y is S;
U is selected from halo, $-OR^{10}$, $-NR^{14}R^{15}$, nitro, cyano, $-COOR^{10}$, $-COR^{13}$, $-OCOR^{13}$, $-CONR^{14}R^{15}$, $-N(R^{14})COR^{13}$, $-SO_3H$, $-SO_2NR^{14}R^{15}$, $-C(=NR^{17})NR^{14}R^{15}$, $-N(R^{14})SO_2R^{16}$, and a 5 or 6-membered heterocyclic group;
A is a phenyl fused ring moiety or a pyridyl fused ring moiety, wherein when A is a phenyl ring moiety, k is 0-3 and t is 0 or 1 and when A is a pyridyl ring moiety, k is 0-2 and t is 0;
$W^1$ is selected from $C_3$-$C_8$ cycloalkyl, aryl and Het, wherein said $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, $-C_0$-$C_6$ alkyl-$CO_2R^{10}$, $-C_0$-$C_6$ alkyl-C(O)$SR^{10}$, $-C_0$-$C_6$ alkyl-$CONR^{11}R^{12}$, $-C_0$-$C_6$ alkyl-$COR^{13}$, $-C_0$-$C_6$ alkyl-$NR^{11}R^{12}$, $-C_0$-$C_6$ alkyl-$SR^{10}$, $-C_0$-$C_6$ alkyl-$OR^{10}$, $-C_0$-$C_6$ alkyl-$SO_3H$, $-C_0$-$C_6$ alkyl-$SO_2NR^{11}R^{12}$, $-C_0$-$C_6$ alkyl-$SO_2R^{10}$, $-C_0$-$C_6$ alkyl-$SOR^{13}$, $-C_0$-$C_6$ alkyl-$OCOR^{13}$, $-C_0$-$C_6$ alkyl-OC(O)$NR^{11}R^{12}$, $-C_0$-$C_6$ alkyl-OC(O)$OR^{13}$, $-C_0$-$C_6$ alkyl-$NR^{11}C(O)OR^{13}$, $-C_0$-$C_6$ alkyl-$NR^{11}C(O)NR^{11}R^{12}$, and $-C_0$-$C_6$ alkyl-$NR^{11}COR^{13}$, where said $C_1$-$C_6$ alkyl, is optionally unsubstituted or substituted by one or more halo substituents;
$W^2$ is selected from H, halo, $C_1$-$C_6$ alkyl, $C_2$-$C_6$ alkenyl, $C_2$-$C_6$ alkynyl, $-C_0$-$C_6$ alkyl-$NR^{11}R^{12}$, $-C_0$-$C_6$ alkyl-$SR^{10}$, $-C_0$-$C_6$ alkyl-$OR^{10}$, $-C_0$-$C_6$ alkyl-$CO_2R^{10}$, $-C_0$-$C_6$ alkyl-C(O)$SR^{10}$, $-C_0$-$C_6$ alkyl-$CONR^{11}R^{12}$, $-C_0$-$C_6$ alkyl-$COR^{13}$, $-C_0$-$C_6$ alkyl-$OCOR^{13}$, $-C_0$-$C_6$ alkyl-$OCONR^{11}R^{12}$, $-C_0$-$C_6$ alkyl-$NR^{11}CONR^{11}R^{12}$, $-C_0$-$C_6$ alkyl-$NR^{11}COR^{13}$, $-C_0$-$C_6$ alkyl-Het, $-C_0$-$C_6$ alkyl-Ar and $-C_0$-$C_6$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said $-C_0$-$C_6$ alkyl-Het, $-C_0$-$C_6$ alkyl-Ar and $-C_0$-$C_6$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, $-C_0$-$C_6$ alkyl-$CO_2R^{10}$, $-C_0$-$C_6$ alkyl-C(O)$SR^{10}$, $-C_0$-$C_6$ alkyl-$CONR^{11}R^{12}$, $-C_0$-$C_6$ alkyl-$COR^{13}$, $-C_0$-$C_6$ alkyl-$NR^{11}R^{12}$, $-C_0$-$C_6$ alkyl-$SR^{10}$, $-C_0$-$C_6$ alkyl-$OR^{10}$, $-C_0$-$C_6$ alkyl-$SO_3H$, $-C_0$-$C_6$ alkyl-$SO_2NR^{11}R^{12}$, $-C_0$-$C_6$ alkyl-$SO_2R^{10}$, $-C_0$-$C_6$ alkyl-$SOR^{13}$, $-C_0$-$C_6$ alkyl-$OCOR^{13}$, $-C_0$-$C_6$ alkyl-OC(O)$NR^{11}R^{12}$, $-C_0$-$C_6$ alkyl-OC(O)$OR^{13}$, $-C_0$-$C_6$ alkyl-$NR^{11}C(O)OR^{13}$, $-C_0$-$C_6$ alkyl-$NR^{11}C(O)NR^{11}R^{12}$, and —$C_0$-$C_6$ alkyl-$NR^{11}COR^{13}$, where said $C_1$-$C_6$ alkyl, is optionally unsubstituted or substituted by one or more halo substituents;

$W^3$ is selected from the group consisting of: H, halo, $C_1$-$C_6$ alkyl, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$CO_2R^{10}$, —$C_0$-$C_6$ alkyl-$C(O)SR^{10}$, —$C_0$-$C_6$ alkyl-$CONR^{11}R^{12}$, —$C_0$-$C_6$ alkyl-$COR^{13}$, —$C_0$-$C_6$ alkyl-$OCOR^{13}$, —$C_0$-$C_6$ alkyl-$OCONR^{11}R^{12}$, —$C_0$-$C_6$ alkyl-$NR^{11}CONR^{11}R^{12}$, —$C_0$-$C_6$ alkyl-$NR^{11}COR^{13}$, —$C_0$-$C_6$ alkyl-Het, —$C_1$-$C_6$ alkyl-Ar and —$C_1$-$C_6$ alkyl-$C_3$-$C_7$ cycloalkyl, wherein said $C_1$-$C_6$ alkyl is optionally unsubstituted or substituted by one or more halo substituents;

Q is selected from $C_3$-$C_8$ cycloalkyl, Ar and Het; wherein said $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_6$ alkyl-$CO_2R^{10}$, —$C_0$-$C_6$ alkyl-$C(O)SR^{10}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$ alkyl-$SO_2NR^{11}R^{12}$, —$C_0$-$C_6$ alkyl-$SO_2R^{10}$, —$C_0$-$C_6$ alkyl-$SOR^{13}$, —$C_0$-$C_6$ alkyl-$OCOR^{13}$, —$C_0$-$C_6$ alkyl-$OC(O)NR^{11}R^{12}$, —$C_0$-$C_6$ alkyl-$OC(O)OR^{13}$, —$C_0$-$C_6$ alkyl-$NR^{11}C(O)OR^{13}$, —$C_0$-$C_6$ alkyl-$NR^{11}C(O)NR^{11}R^{12}$, and —$C_0$-$C_6$ alkyl-$NR^{11}COR^{13}$, where said $C_1$-$C_6$ alkyl is optionally unsubstituted or substituted by one or more halo substituents;

p is 0-8;

n is 2-8;

m is 0 or 1;

q is 0 or 1;

t is 0 or 1;

each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-$NR^{11}R^{12}$, —$C_0$-$C_6$ alkyl-$OR^{10}$, —$C_0$-$C_6$ alkyl-$SR^{10}$, —$C_0$-$C_6$ alkyl-Het, —$C_1$-$C_6$ alkyl-Ar and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where said $C_1$-$C_6$ alkyl is optionally unsubstituted or substituted by one or more halo substituents;

each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{10}$, —$C_0$-$C_6$ alkyl-$C(O)SR^{10}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$ alkyl-$SO_2NR^{11}R^{12}$, —$C_0$-$C_6$ alkyl-$SO_2R^{10}$, —$C_0$-$C_6$ alkyl-$SOR^{13}$, —$C_0$-$C_6$ alkyl-$OCOR^{13}$, —$C_0$-$C_6$ alkyl-$OC(O)NR^{11}R^{12}$, —$C_0$-$C_6$ alkyl-$OC(O)OR^{13}$, —$C_0$-$C_6$ alkyl-$NR^{11}C(O)OR^{13}$, —$C_0$-$C_6$ alkyl-$NR^{11}C(O)NR^{11}R^{12}$, and —$C_0$-$C_6$ alkyl-$NR^{11}COR^{13}$, wherein said $C_1$-$C_6$ alkyl is optionally unsubstituted or substituted by one or more halo substituents;

each $R^4$ and $R^5$ is independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^6$ and $R^7$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^8$ and $R^9$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^{10}$ is selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

each $R^{11}$ and each $R^{12}$ are independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl, or $R^{11}$ and $R^{12}$ together with the nitrogen to which they are attached form a 4-7 membered heterocyclic ring which optionally contains one or more additional heteroatoms selected from N, O, and S;

$R^{13}$ is selected from $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

$R^{14}$ and $R^{15}$ are each independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-O—Ar, —$C_0$-$C_6$ alkyl-O-Het, —$C_0$-$C_6$ alkyl-O—$C_3$-$C_7$ cycloalkyl, —$C_0$-$C_6$ alkyl-$S(O)_x$-$C_1$-$C_6$ alkyl, —$C_0$-$C_6$ alkyl-$S(O)_x$—Ar, —$C_0$-$C_6$ alkyl-$S(O)_x$-Het, —$C_0$-$C_6$ alkyl-$S(O)_x$-$C_3$-$C_7$ cycloalkyl, —$C_0$-$C_6$ alkyl-NH—Ar, —$C_0$-$C_6$ alkyl-NH—Het, —$C_0$-$C_6$ alkyl-NH—$C_3$-$C_7$ cycloalkyl, —$C_0$-$C_6$ alkyl-N($C_1$-$C_4$ alkyl)-Ar, —$C_0$-$C_6$ alkyl-N($C_1$-$C_4$ alkyl)-Het, —$C_0$-$C_6$ alkyl-N($C_1$-$C_4$ alkyl)-$C_3$-$C_7$ cycloalkyl, —$C_0$-$C_6$ alkyl-Ar, —$C_0$-$C_6$ alkyl-Het and —$C_0$-$C_6$ alkyl-$C_3$-$C_7$ cycloalkyl, where x is 0, 1 or 2, or $R^{14}$ and $R^{15}$, together with the nitrogen to which they are attached, form a 4-7 membered heterocyclic ring which optionally contains one or more additional heteroatoms selected from N, O, and S, wherein said $C_1$-$C_6$ alkyl is optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$ alkyl), unsubstituted —$OC_1$-$C_6$ alkyl, —$CO_2H$, —$CO_2$(unsubstituted $C_1$-$C_6$ alkyl), —$CONH_2$, —CONH(unsubstituted $C_1$-$C_6$ alkyl), —CON(unsubstituted $C_1$-$C_6$ alkyl)(unsubstituted $C_1$-$C_6$ alkyl), —$SO_3H$, —$SO_2NH_2$, —$SO_2NH$(unsubstituted $C_1$-$C_6$ alkyl) and —$SO_2N$(unsubstituted $C_1$-$C_6$ alkyl)(unsubstituted $C_1$-$C_6$ alkyl);

$R^{16}$ is $C_1$-$C_6$ alkyl, —$C_0$-$C_6$ alkyl-Ar or —$C_0$-$C_6$ alkyl-Het; and $R^{17}$ is H, $C_1$-$C_6$ alkyl, —$C_0$-$C_6$ alkyl-Ar or —$C_0$-$C_6$ alkyl-Het;

or a pharmaceutically acceptable salt or solvate thereof.

Unless otherwise provided, each alkyl, alkoxy, alkenyl, alkynyl, cycloalkyl, aryl or Het (including any 3-5-membered, 4-7-membered, 5-6-membered or 5-7-membered carbocyclic or heterocyclic rings or ring moieties) herein is independently unsubstituted or substituted with one ore more substituents defined hereinbelow.

Also included within the scope of this invention are methods for preparing compounds of this invention, or pharmaceutically acceptable salts or solvates thereof and methods of using the same. The present invention also provides pharmaceutical compositions comprising a compound of this invention, or a pharmaceutically acceptable salt or solvate thereof.

LXR mediated diseases or conditions include inflammation, cardiovascular disease and atherosclerosis. Accordingly, the methods of this invention further comprise methods for increasing reverse cholesterol transport, inhibiting cholesterol absorption, and decreasing inflammation. The present invention also provides pharmaceutical compositions comprising a compound of this invention, or a pharmaceutically acceptable salt or solvate thereof.

DETAILED DESCRIPTION OF THE INVENTION

As used herein, the term "alkyl" represents a straight-or branched-chain saturated hydrocarbon, containing 1 to 10 carbon atoms, unless otherwise provided, which may be unsubstituted or substituted by one or more of the substituents described below. Exemplary alkyls include, but are not limited to methyl (Me), ethyl (Et), n-propyl, isopropyl, n-butyl, isobutyl, t-butyl, n-pentyl, neopentyl and hexyl and structural isomers thereof. Any "alkyl" herein may be optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$ alkyl), unsubstituted —$OC_1$-$C_6$ alkyl, and —$CO_2H$.

When combined with another substituent term (e.g., aryl or cycloalkyl as in -alkyl-Ar or -alkyl-cycloalkyl), the "alkyl" term therein refers to an alkylene moiety, that is, an unsubstituted divalent straight-or branched-chain saturated hydrocarbon moiety, containing 1 to 10 carbon atoms, unless otherwise provided. For example, the term "—$C_0$-$C_6$ alkyl-Ar", where C is 1-6 is intended to mean the radical -alkyl-aryl (e.g., —$CH_2$-aryl or —$CH(CH_3)$-aryl) and is represented by the bonding arrangement present in a benzyl group. The term "$C_0$ alkyl" in a moiety, such as —$C_0$-$C_6$ alkyl-Ar or —O—($C_0$-$C_6$ alkyl)-Ar, provides for no alkyl/alkylene group being present in the moiety. Thus, when C is zero, —$C_0$-$C_6$ alkyl-Ar is equivalent to —Ar and —O—($C_0$-$C_6$ alkyl)-Ar is equivalent to —O—Ar.

As used herein, the term "alkenyl" represents a straight-or branched-chain hydrocarbon, containing 2 to 10 carbon atoms, unless otherwise provided, and one or more carbon-carbon double bonds. Alkenyl groups may be unsubstituted or substituted by one or more of the substituents described below. Exemplary alkenyls include, but are not limited ethenyl, 1-propenyl, 2-propenyl, 1-butenyl, 2-butenyl, isobutenyl, butadienyl, pentenyl and hexenyl and structural isomers thereof. Both cis (Z) and trans (E) isomers of each double bond that may be present in the compounds of this invention are included within the scope of this invention. Any "alkenyl" herein may be optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$ alkyl), unsubstituted —$OC_1$-$C_6$ alkyl, and —$CO_2H$.

As used herein, the term "alkynyl" represents a straight-or branched-chain hydrocarbon, containing 2 to 10 carbon atoms, unless otherwise provided, and one or more carbon-carbon triple bonds and, optionally, one or more carbon-carbon double bonds. Both cis (Z) and trans (E) isomers of each double bond that may be present in the compounds of this invention are included within the scope of this invention. Exemplary alkynyls include, but are not limited ethynyl, propynyl (propargyl, isopropynyl), 1-butynyl, 2-butynyl, 3-butynyl, pentynyl and hexynyl and structural isomers thereof. Any "alkynyl" herein may be optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$ alkyl), unsubstituted —$OC_1$-$C_6$ alkyl, and —$CO_2H$.

For the purposes of this invention, when an alkenyl or alkynyl group is a substituent on an oxygen, nitrogen or sulfur atom (e.g., as in oxy (—OR), thio (—SR), ester (—$CO_2R$ or —C(O)SR), amino (—NRR) or amido (—CONRR) moieties and the like), it is understood that a double or triple bond of the alkenyl or alkynyl group is not located on carbons that are α,β to the oxygen, nitrogen or sulfur atom. Compounds containing ene-amino or enol-type moieties (—NR—CR=CR— or —O—CR=CR—) are not intended to be included within the scope of this invention.

"Cycloalkyl" represents a non-aromatic monocyclic, bicyclic, or tricyclic hydrocarbon containing from 3 to 10 carbon atoms which may be unsubstituted or substituted by one or more of the substituents described below and may be saturated or partially unsaturated. Exemplary cycloalkyls include monocyclic rings having from 3-7, preferably 3-6, carbon atoms, such as cyclopropyl, cyclobutyl, cyclopentyl, cyclopentenyl, cyclopentadienyl, cyclohexyl, cyclohexenyl and cycloheptyl. Any "cycloalkyl" herein may be optionally substituted by one or more of the substituents independently selected from the group halo, cyano, $C_1$-$C_6$ alkyl (which specifically includes $C_1$-$C_6$ haloalkyl, —$C_0$-$C_6$ alkyl-OH, —$C_0$-$C_6$ alkyl-SH and —$C_0$-$C_6$ alkyl-NR'R"), $C_3$-$C_6$ alkenyl, oxo, —$OC_1$-$C_6$alkyl, —$OC_1$-$C_6$ alkenyl, —$C_0$-$C_6$ alkyl-COR', —$C_1$-$C_6$ alkyl-$CO_2$R', —$C_0$-$C_6$ alkyl-CONR'R", —$OC_0$-$C_6$ alkyl-$CO_2$H, —$OC_2$-$C_6$ alkyl-NR'R", and —$C_0$-$C_6$ alkyl-$SO_2$NR'R", wherein each R' and R" are independently selected from H and unsubstituted $C_1$-$C_6$ alkyl.

The terms "Ar" or "aryl" as used herein interchangeably at all occurrences mean a substituted or unsubstituted carbocyclic aromatic group, which may be optionally fused to another carbocyclic aromatic group moiety or to a cycloalkyl group moiety, which may be optionally substituted or unsubstituted. Examples of suitable Ar or aryl groups include phenyl, naphthyl indenyl, 1-oxo-1H-indenyl and tetrahydronaphthyl. Any "Ar", "aryl" or "phenyl" herein may be optionally unsubstituted or substituted by one or more of the substituents independently selected from the group halo, cyano, $C_1$-$C_6$ alkyl (which specifically includes $C_1$-$C_6$ haloalkyl, —$C_0$-$C_6$ alkyl-OH, —$C_0$-$C_6$ alkyl-SH and —$C_0$-$C_6$ alkyl-NR'R"), $C_3$-$C_6$ alkenyl, oxo, —$OC_1$-$C_6$alkyl, —$OC_1$-$C_6$ alkenyl, —$C_0$-$C_6$ alkyl-COR', —$C_0$-$C_6$ alkyl-$CO_2$R', —$C_0$-$C_6$ alkyl-CONR'R", —$OC_0$-$C_6$ alkyl-$CO_2$H, —$OC_2$-$C_6$ alkyl-NR'R", —$C_0$-$C_6$ alkyl-C(=NR')NR'R", and —$C_0$-$C_6$ alkyl-$SO_2$NR'R", wherein each R' and R" are independently selected from H and unsubstituted $C_1$-$C_6$ alkyl.

The term "Het" as used herein means a stable 5- to 7-membered monocyclic, a stable 7- to 10-membered bicyclic, or a stable 11- to 18-membered tricyclic heterocyclic ring group, all of which are saturated, unsaturated or aromatic, and consist of carbon atoms and from one to three heteroatoms selected from N, O and S, and which includes bicyclic and tricyclic rings containing one or more fused cycloalkyl, aryl (e.g., phenyl) or heteroaryl (aromatic Het) ring moieties. As used herein the term "Het" is also intended to encompass heterocyclic groups containing nitrogen and/or sulfur where the nitrogen or sulfur heteroatoms are optionally oxidized or the nitrogen heteroatom is optionally quaternized. The heterocyclic group may be attached at any heteroatom or carbon atom that results in the creation of a stable structure. Any "Het" herein may be optionally unsubstituted or substituted by one or more of the substituents independently selected from the group halo, cyano, $C_1$-$C_6$ alkyl (which specifically includes $C_1$-$C_6$ haloalkyl, —$C_0$-$C_6$ alkyl-OH, —$C_0$-$C_6$ alkyl-SH and —$C_0$-$C_6$ alkyl-NR'R"), $C_3$-$C_6$ alkenyl, oxo, —$OC_1$-$C_6$alkyl, —$OC_1$-$C_6$ alkenyl, —$C_0$-$C_6$ alkyl-COR', —$C_0$-$C_6$ alkyl-$CO_2$R', —$C_0$-$C_6$ alkyl-CONR'R", —$OC_0$-$C_6$ alkyl-$CO_2$H, —$OC_2$-$C_6$ alkyl-NR'R", —$C_0$-$C_6$ alkyl-C(=NR')NR'R" and —$C_0$-$C_6$ alkyl- SO$_2$NR'R", wherein each R' and R" are independently selected from H and unsubstituted C$_1$-C$_6$ alkyl.

Examples of such heterocyclic groups include, but are not limited to piperidinyl, piperazinyl, 2-oxopiperazinyl, 2-oxopiperidinyl, 2-oxopyrrolodinyl, 2-oxoazepinyl, azepanyl, pyrrolyl, 4-piperidonyl, pyrrolidinyl, pyrazolyl, pyrazolidinyl, imidazolyl, pyridinyl, pyrazinyl, oxazolidinyl, oxazolinyl, oxazolyl, isoxazolyl, morpholinyl, thiazolidinyl, thiazolinyl, thiazolyl, 1,3-benzodioxolyl (e.g., methylenedioxy-substituted phenyl), 1,4-benzodioxolyl, quinuclidinyl, indolyl, quinolinyl, isoquinolinyl, benzimidazolyl, benzopyranyl, benzoxazolyl, furyl, pyranyl, tetrahydrofuryl, tetrahydropyranyl, thienyl, benzoxazolyl, benzofuranyl, benzothienyl, dihydrobenzofuranyl, dihydrobenzothienyl, dihydroindolyl, tetrazolyl, thiamorpholinyl sulfoxide, thiamorpholinyl sulfone, and oxadiazolyl, as well as triazolyl, thiadiazolyl, oxadiazolyl, isoxazolyl, isothiazolyl, imidazolyl, pyridazinyl, pyrimidinyl and triazinyl which are available by routine chemical synthesis and are stable.

Examples of the 4-7 membered heterocyclic rings useful in the compounds of this invention, include, but are not limited to azetidinyl, piperidinyl, piperazinyl, 2-oxopiperazinyl, 2-oxopiperidinyl, 2-oxopyrrolodinyl, azepanyl, pyrrolyl, 4-piperidonyl, pyrrolidinyl, pyrazolyl, pyrazolidinyl, imidazolyl, pyridinyl, pyrazinyl, oxazolidinyl, oxazolinyl, oxazolyl, isoxazolyl, morpholinyl, thiazolidinyl, thiazolinyl, thiazolyl, furyl, pyranyl, tetrahydrofuryl, tetrahydropyranyl, thienyl, tetrazolyl, thiamorpholinyl sulfoxide, thiamorpholinyl sulfone, and oxadiazolyl, as well as triazolyl, thiadiazolyl, oxadiazolyl, isoxazolyl, isothiazolyl, imidazolyl, pyridazinyl, pyrimidinyl and triazinyl which are available by routine chemical synthesis and are stable. The 4-7 membered heterocyclic group may be optionally unsubstituted or substituted by one or more of the substituents independently selected from the group halo, cyano, C$_1$-C$_6$ alkyl (which specifically includes C$_1$-C$_6$ haloalkyl, —C$_0$-C$_6$ alkyl-OH, —C$_0$-C$_6$ alkyl-SH and —C$_0$-C$_6$ alkyl-NR'R"), C$_3$-C$_6$ alkenyl, oxo, —OC$_1$-C$_6$alkyl, —OC$_1$-C$_6$ alkenyl, —C$_0$-C$_6$ alkyl-COR', —C$_0$-C$_6$ alkyl-CO$_2$R', —C$_0$-C$_6$ alkyl-CONR'R", —OC$_0$-C$_6$ alkyl-CO$_2$H, —OC$_2$-C$_6$ alkyl-NR'R", —C$_0$-C$_6$ alkyl-C(=NR')NR'R" and —C$_0$-C$_6$ alkyl-SO$_2$NR'R", wherein each R' and R" are independently selected from H and unsubstituted C$_1$-C$_6$ alkyl.

Examples of 5 or 6 membered heterocyclic groups include, but are not limited to piperidinyl, piperazinyl, 2-oxopiperazinyl, 2-oxopiperidinyl, 2-oxopyrrolodinyl, pyrrolyl, 4-piperidonyl, pyrrolidinyl, pyrazolyl, pyrazolidinyl, imidazolyl, pyridinyl, pyrazinyl, oxazolidinyl, oxazolinyl, oxazolyl, isoxazolyl, morpholinyl, thiazolidinyl, thiazolinyl, thiazolyl, furyl, pyranyl, tetrahydrofuryl, tetrahydropyranyl, thienyl, tetrazolyl, thiamorpholinyl sulfoxide, thiamorpholinyl sulfone, and oxadiazolyl, as well as triazolyl, thiadiazolyl, oxadiazolyl, isoxazolyl, isothiazolyl, imidazolyl, pyridazinyl, pyrimidinyl and triazinyl which are available by routine chemical synthesis and are stable. The 5-6 membered heterocyclic group may be attached at any heteroatom or carbon atom that results in the creation of a stable structure. The 5-6 membered heterocyclic group may be optionally unsubstituted or substituted by one or more of the substituents independently selected from the group halo, cyano, C$_1$-C$_6$ alkyl (which specifically includes C$_1$-C$_6$ haloalkyl, —C$_0$-C$_6$ alkyl-OH, —C$_0$-C$_6$ alkyl-SH and —C$_0$-C$_6$ alkyl-NR'R"), C$_3$-C$_6$ alkenyl, oxo, —OC$_1$-C$_6$alkyl, —OC$_1$-C$_6$ alkenyl, —C$_0$-C$_6$ alkyl-COR', —C$_0$-C$_6$ alkyl-CO$_2$R', —C$_0$-C$_6$ alkyl-CONR'R", —OC$_0$-C$_6$ alkyl-CO$_2$H, —OC$_2$-C$_6$ alkyl-NR'R", —C$_0$-C$_6$ alkyl-C(=NR')NR'R" and —C$_0$-C$_6$ alkyl-SO$_2$NR'R", wherein each R' and R" are independently selected from H and unsubstituted C$_1$-C$_6$ alkyl.

In the compounds of this invention, group A is defined as a phenyl or pyridyl fused ring moiety and is exemplified by the following:

Group A fused ring moiety:

phenyl:

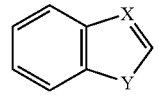

pyridyl:

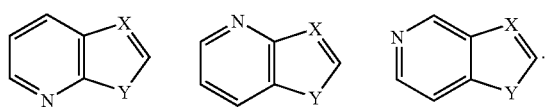

The terms "halogen" and "halo" represent chloro, fluoro, bromo or iodo substituents. "Alkoxy" is intended to mean the radical —OR$_a$, where R$_a$ is an alkyl group, wherein alkyl is as defined above, provided that —O—C$_1$ alkyl may be optionally substituted by one or more of the substituents independently selected from the group halo and —CO$_2$H. Exemplary alkoxy groups include methoxy, ethoxy, propoxy, and the like. "Phenoxy" is intended to mean the radical —OR$_{ar}$, where R$_{ar}$ is a phenyl group. "Acetoxy" is intended to mean the radical —O—C(=O)-methyl. "Benzoyloxy" is intended to mean the radical —O—C(=O)-phenyl. "Oxo" is intended to mean the keto diradical =O, such as present on a pyrrolidin-2-one ring.

If a substituent described herein is not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful as an intermediate compound in the methods of this invention or is a desired substituent in a target compound.

The term "pharmaceutically acceptable salt" is intended to describe a salt that retains the biological effectiveness of the free acid or base of a specified compound and is not biologically or otherwise undesirable.

If an inventive compound is a base, a desired salt may be prepared by any suitable method known in the art, including treatment of the free base with an inorganic acid, such as hydrochloric acid, hydrobromic acid, sulfuric acid, sulfamic acid, nitric acid, phosphoric acid, metaphosphoric acid and the like, or with an organic acid, such as acetic acid, trifluoroacetic acid, formic acid, maleic acid, lactic acid, succinic acid, mandelic acid, fumaric acid, malonic acid, malic acid, pyruvic acid, oxalic acid, glycolic acid, citric acid, tartaric acid, gluconic acid, glutaric acid, lactobionic, orotic, cholic, a pyranosidyl acid, such as glucuronic acid or galacturonic acid, an amino acid, such as aspartic acid or glutamic acid, an aromatic acid, such as benzoic acid, salicylic acid, cinnamic acid, pamoic acid or 1-hydroxy-2-naphthoic acid, a sulfonic acid, such as benzenesulfonic acid, p-toluenesulfonic acid, naphthalenesulfonic acid, methanesulfonic acid, ethanesulfonic acid or the like. Additional examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycollates, tartrates mandelates, and sulfonates, such as xylenesulfonates, methanesulfonates, propanesulfonates, naphthalene-1-sulfonates and naphthalene-2-sulfonates. Embodiments of a pharmaceutically acceptable salt (e.g., the hydrochloride salt) of the compounds of this invention are provided in the Examples.

If an inventive compound is an acid, a desired salt may be prepared by any suitable method known to the art, including treatment of the free acid with an excess of an inorganic or organic alkaline reagent. Illustrative examples of suitable salts include spalts derived from ammonia; primary, secondary, tertiary amines (including secondary and tertiary cyclic amines), such as ethylene diamine, dicyclohexylamine, ethanolamine, piperidine, morpholine, and piperazine; salts derived from amino acids such as glycine and arginine; as well as salts derived from an alkali metal, alkaline earth metal, or ammonium hydroxide, carbonate, alkoxide or sulfate, such as sodium hydroxide, sodium carbonate, sodium bicarbonate, sodium sulfate, etc., and corresponding alkaline salts containing, for example, $Li^+$, $K^+$, $Ca^{++}$, $Mg^{++}$ and $NH_4^+$ cations.

Because the compounds of this invention may contain both acid and base moieties, pharmaceutically acceptable salts may be prepared by treating these compounds with an alkaline reagent or an acid reagent, respectively. Accordingly, this invention also provides for the conversion of one pharmaceutically acceptable salt of a compound of this invention, e.g., a hydrochloride salt, into another pharmaceutically acceptable salt of a compound of this invention, e.g., a mesylate salt or a sodium salt.

The term "solvate" is intended to mean a pharmaceutically acceptable solvate form of a specified compound of this invention, or a salt thereof, that retains the biological effectiveness of such compound. Examples of solvates include compounds of the invention in combination with water, isopropanol, ethanol, methanol, DMSO, ethyl acetate, acetic acid, or ethanolamine. In the case of compounds, salts, or solvates that are solids, it is understood by those skilled in the art that the inventive compounds, salts, or solvates may exist in different crystal forms, all of which are intended to be within the scope of the present invention and specified formulas.

Also included within the scope of this invention are prodrugs of the compounds of this invention. The ester compounds of this invention, wherein X is other than —OH, may be considered prodrugs. Such ester compounds may be converted to compounds that are active as LXR modulators and may be, themselves, active as LXR modulators. The term "prodrug" is intended to mean a compound that is converted under physiological conditions, e.g., by solvolysis or metabolically, to a compound according to this invention that is pharmaceutically active. A prodrug may be a derivative of one of the compounds of this invention that contains a carboxylic or phosphoric acid ester or amide moiety that may be cleaved under physiological conditions. A prodrug containing such a moiety may be prepared according to conventional procedures, for example, by treatment of a compound of this invention containing an amino, amido or hydroxyl moiety with a suitable derivatizing agent, for example, a carboxylic or phosphoric acid halide or acid anhydride, or by converting a carboxyl moiety of a compound of this invention to an ester or amide. Prodrugs of the compounds of this invention may be determined using techniques known in the art, for example, through metabolic studies. See, e.g., "Design of Prodrugs," (H. Bundgaard, Ed.) 1985, Elsevier Publishers B. V., Amsterdam, The Netherlands.

It will be appreciated by those skilled in the art that the compounds of this invention may exist in different tautomeric forms. All tautomeric forms of the compounds described herein are intended to be encompassed within the scope of the present invention.

The compounds of this invention may contain at least one chiral center and may exist as single stereoisomers (e.g., single enantiomers), mixtures of stereoisomers (e.g., any mixture of enantiomers or diastereomers) or racemic mixtures thereof. All such single stereoisomers, mixtures and racemates are intended to be encompassed within the broad scope of the present invention. Compounds identified herein as single stereoisomers are meant to describe compounds that are present in a form that are at least 90% enantiomerically pure. Where the stereochemistry of the chiral carbons present in the chemical structures illustrated herein is not specified, the chemical structure is intended to encompass compounds containing either stereoisomer of each chiral center present in the compound. Such compounds may be obtained synthetically, according to the procedures described herein using optically pure (enantiomerically pure) or substantially optically pure materials. Alternatively, these compounds may be obtained by resolution/separation of a mixture of stereoisomers, including racemic mixtures, using conventional procedures. Exemplary methods that may be useful for the resolution/separation of mixtures of stereoisomers include chromatography and crystallization/re-crystallization. Other useful methods may be found in "*Enantiomers, Racemates, and Resolutions*," J. Jacques et al., 1981, John Wiley and Sons, New York, N.Y., the disclosure of which is incorporated herein by reference.

In one embodiment of this invention, the group U—$(CR^1R^2)_p$— is located on the A-ring moiety in a position that is meta or para to the —Y—$(CR^4R^5)_n$— moiety. Preferably, the group U—$(CR^1R^2)_p$— is located in a position that is meta to the —Y—$(CR^4R^5)_n$— moiety.

In another embodiment, this invention is directed to a compound of Formula II:

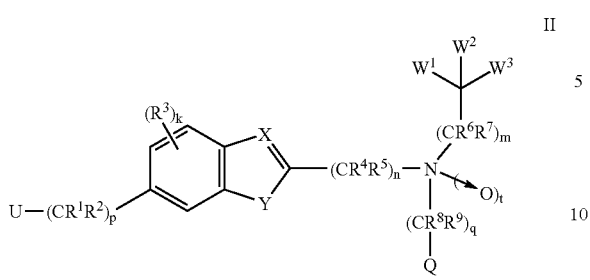

wherein:

X is CH or N;

Y is O, or S;

U is selected from halo, —$OR^{10}$, —$NR^{14}R^{15}$, cyano, —$COOR^{10}$, —$OCOR^{13}$, —$CONR^{14}R^{15}$, —$N(R^{14})COR^{13}$, —$SO_2NR^{14}R^{15}$, —$C(=NH)NR^{14}R^{15}$, and a 5 or 6-membered heterocyclic group;

A is a phenyl fused ring moiety, wherein k is 0 or 1;

$W^1$ is selected from $C_3$-$C_8$ cycloalkyl, aryl and Het, wherein said $C_3$-$C_8$ cycloalkyl, Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_4$ alkyl-$CO_2R^{10}$, —$C_0$-$C_4$ alkyl-C(O)$SR^{10}$, —$C_0$-$C_4$ alkyl-$CONR^{11}R^{12}$, —$C_0$-$C_4$ alkyl-$COR^{13}$, —$C_0$-$C_4$ alkyl-$NR^{11}R^{12}$, —$C_0$-$C_4$ alkyl-$SR^{10}$, —$C_0$-$C_4$ alkyl-$OR^{10}$, —$C_0$-$C_4$ alkyl-$SO_3H$, —$C_0$-$C_4$ alkyl-$SO_2NR^{11}R^{12}$, —$C_0$-$C_4$ alkyl-$SO_2R^{10}$, —$C_0$-$C_4$ alkyl-$SOR^{13}$, —$C_0$-$C_4$ alkyl-$OCOR^{13}$, —$C_0$-$C_4$ alkyl-OC(O)$NR^{11}R^{12}$, —$C_0$-$C_4$ alkyl-OC(O)$OR^{13}$, —$C_0$-$C_4$ alkyl-$NR^{11}C(O)OR^{13}$, —$C_0$-$C_4$ alkyl-$NR^{11}C(O)NR^{11}R^{12}$, and —$C_0$-$C_4$ alkyl-$NR^{11}COR^{13}$, where said $C_1$-$C_6$ alkyl is optionally unsubstituted or substituted by one or more halo substituents;

$W^2$ is selected from H, halo, $C_1$-$C_6$ alkyl, $C_2$-$C_6$ alkenyl, $C_2$-$C_6$ alkynyl, —$C_0$-$C_4$ alkyl-$NR^{11}R^{12}$, —$C_0$-$C_4$ alkyl-$SR^{10}$, —$C_0$-$C_4$ alkyl-$OR^{10}$, —$C_0$-$C_4$ alkyl-$CO_2R^{10}$, —$C_0$-$C_4$ alkyl-C(O)$SR^{10}$, —$C_0$-$C_4$ alkyl-$CONR^{11}R^{12}$, —$C_0$-$C_4$ alkyl-$COR^{13}$, —$C_0$-$C_4$ alkyl-$OCOR^{13}$, —$C_0$-$C_4$ alkyl-$OCONR^{11}R^{12}$, —$C_0$-$C_4$ alkyl-$NR^{11}CONR^{11}R^{12}$, —$C_0$-$C_4$ alkyl-$NR^{11}COR^{13}$, —$C_0$-$C_4$ alkyl-Het, —$C_0$-$C_4$ alkyl-Ar and —$C_0$-$C_4$ alkyl-$C_3$-$C_7$ cycloalkyl, wherein said $C_1$-$C_6$ alkyl is optionally unsubstituted or substituted by one or more halo substituents, and wherein the $C_3$-$C_7$ cycloalkyl, Ar and Het moieties of said —$C_0$-$C_4$ alkyl-Het, —$C_0$-$C_4$ alkyl-Ar and —$C_0$-$C_4$ alkyl-$C_3$-$C_7$ cycloalkyl are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_4$ alkyl-$CO_2R^{10}$, —$C_0$-$C_4$ alkyl-C(O)$SR^{10}$, —$C_0$-$C_4$ alkyl-$CONR^{11}R^{12}$, —$C_0$-$C_4$ alkyl-$COR^{13}$, —$C_0$-$C_4$ alkyl-$NR^{11}R^{12}$, —$C_0$-$C_4$ alkyl-$SR^{10}$, —$C_0$-$C_4$ alkyl-$OR^{10}$, —$C_0$-$C_4$ alkyl-$SO_3H$, —$C_0$-$C_4$ alkyl-$SO_2NR^{11}R^{12}$, —$C_0$-$C_4$ alkyl-$SO_2R^{10}$, —$C_0$-$C_4$ alkyl-$SOR^{13}$, —$C_0$-$C_4$ alkyl-$OCOR^{13}$, —$C_0$-$C_4$ alkyl-OC(O)$NR^{11}R^{12}$, —$C_0$-$C_4$ alkyl-OC(O)$OR^{13}$, —$C_0$-$C_4$ alkyl-$NR^{11}C(O)OR^{13}$, —$C_0$-$C_4$ alkyl-$NR^{11}C(O)NR^{11}R^{12}$, and —$C_0$-$C_4$ alkyl-$NR^{11}COR^{13}$, where said $C_1$-$C_6$ alkyl is optionally unsubstituted or substituted by one or more halo substituents;

$W^3$ is selected from the group consisting of: H, halo, $C_1$-$C_6$ alkyl, —$C_0$-$C_4$ alkyl-$NR^{11}R^{12}$, —$C_0$-$C_4$ alkyl-$SR^{10}$, —$C_0$-$C_4$ alkyl-$OR^{10}$, —$C_0$-$C_4$ alkyl-$CO_2R^{10}$, —$C_0$-$C_4$ alkyl-C(O)$SR^{10}$, —$C_0$-$C_4$ alkyl-$CONR^{11}R^{12}$, —$C_0$-$C_4$ alkyl-$COR^{13}$, —$C_0$-$C_4$ alkyl-$OCOR^{13}$, —$C_0$-$C_4$ alkyl-$OCONR^{11}R^{12}$, —$C_0$-$C_4$ alkyl-$NR^{11}CONR^{11}R^{12}$, —$C_0$-$C_4$ alkyl-$NR^{11}COR^{13}$, —$C_0$-$C_4$ alkyl-Het, —$C_1$-$C_4$ alkyl-Ar and —$C_1$-$C_4$ alkyl-$C_3$-$C_7$ cycloalkyl, wherein said $C_1$-$C_6$ alkyl is optionally unsubstituted or substituted by one or more halo substituents;

Q is Ar or Het; wherein said Ar and Het are optionally unsubstituted or substituted with one or more groups independently selected from halo, cyano, nitro, $C_1$-$C_6$ alkyl, $C_3$-$C_6$ alkenyl, $C_3$-$C_6$ alkynyl, —$C_0$-$C_4$ alkyl-$CO_2R^{10}$, —$C_0$-$C_4$ alkyl-C(O)$SR^{10}$, —$C_0$-$C_4$ alkyl-$CONR^{11}R^{12}$, —$C_0$-$C_4$ alkyl-$COR^{13}$, —$C_0$-$C_4$ alkyl-$NR^{11}R^{12}$, —$C_0$-$C_4$ alkyl-$SR^{10}$, —$C_0$-$C_4$ alkyl-$OR^{10}$, —$C_0$-$C_4$ alkyl-$SO_3H$, —$C_0$-$C_4$ alkyl-$SO_2NR^{11}R^{12}$, —$C_0$-$C_4$ alkyl-$SO_2R^{10}$, —$C_0$-$C_4$ alkyl-$SOR^{13}$, —$C_0$-$C_4$ alkyl-$OCOR^{13}$, —$C_0$-$C_4$ alkyl-OC(O)$NR^{11}R^{12}$, —$C_0$-$C_4$ alkyl-OC(O)$OR^{13}$, —$C_0$-$C_4$ alkyl-$NR^{11}C(O)OR^{13}$, —$C_0$-$C_4$ alkyl-$NR^{11}C(O)NR^{11}R^{12}$, and —$C_0$-$C_4$ alkyl-$NR^{11}COR^{13}$, where said $C_1$-$C_6$ alkyl is optionally unsubstituted or substituted by one or more halo substituents, p is 0-4;

n is 2;

m is 0 or 1;

q is 0 or 1;

t is 0;

each $R^1$ and $R^2$ are independently selected from H, fluoro, $C_1$-$C_6$ alkyl, —$C_0$-$C_4$ alkyl-$OR^{10}$, —$C_0$-$C_4$ alkyl-$SR^{10}$, —$C_1$-$C_4$ alkyl-Het, —$C_1$-$C_4$ alkyl-Ar and —$C_1$-$C_4$ alkyl-$C_3$-$C_7$ cycloalkyl, where said $C_1$-$C_6$ alkyl is optionally unsubstituted or substituted by one or more halo substituents;

each $R^3$ is the same or different and is independently selected from halo, cyano, $C_1$-$C_6$ alkyl, —$C_0$-$C_4$ alkyl-$NR^{11}R^{12}$, —$C_0$-$C_4$ alkyl-$OR^{10}$, —$C_0$-$C_4$ alkyl-$SO_2NR^{11}R^{12}$, and —$C_0$-$C_4$ alkyl-$CO_2H$, wherein said $C_1$-$C_6$ alkyl is optionally unsubstituted or substituted by one or more halo substituents;

each $R^4$ and $R^5$ is independently selected from H, fluoro and $C_1$-$C_6$ alkyl;

$R^6$ and $R^7$ are each independently selected from H, fluoro and $C_1$-$C_6$ alkyl;

$R^8$ and $R^9$ are each independently selected from H, fluoro and $C_1$-$C_6$ alkyl;

$R^{10}$ is selected from H, $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl;

each $R^{11}$ and each $R^{12}$ are independently selected from H, $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl, or $R^{11}$ and $R^{12}$ together with the nitrogen to which they are attached form a 4-7 membered heterocyclic ring which optionally contains one or more additional heteroatoms selected from N, O, and S;

$R^{13}$ is selected from $C_1$-$C_6$ alkyl, —$C_0$-$C_4$ alkyl-Ar, —$C_0$-$C_4$ alkyl-Het and —$C_0$-$C_4$ alkyl-$C_3$-$C_7$ cycloalkyl;

$R^{14}$ and $R^{15}$ are each independently selected from H, $C_1$-$C_6$ alkyl, $C_3$-$C_6$ alkenyl, $C_3$-$C_6$ alkynyl, —$C_0$-$C_4$ alkyl-Ar, —$C_0$-$C_4$ alkyl-Het, —$C_0$-$C_4$ alkyl-$C_3$-$C_7$ cycloalkyl, —$C_0$-$C_4$ alkyl-O—Ar, —$C_0$-$C_4$ alkyl-O-Het, —$C_0$-$C_4$ alkyl-O-$C_3$-$C_7$ cycloalkyl, —$C_0$-$C_4$ alkyl-S(O)$_x$-$C_1$-$C_6$ alkyl, —$C_0$-$C_4$ alkyl-S(O)$_x$—Ar, —$C_0$-$C_4$ alkyl-S(O)$_x$-Het, —$C_0$-$C_4$ alkyl-S(O)$_x$-$C_3$-$C_7$ cycloalkyl, —$C_0$-$C_4$ alkyl-NH—Ar, —$C_0$-$C_4$ alkyl- NH-Het, —$C_0$-$C_4$ alkyl-NH—$C_3$-$C_7$ cycloalkyl, —$C_0$-$C_4$ alkyl-N($C_1$-$C_4$ alkyl)-Ar, —$C_0$-$C_4$ alkyl-N($C_1$-$C_4$ alkyl)-Het, —$C_0$-$C_4$ alkyl-N($C_1$-$C_4$ alkyl)-$C_3$-$C_7$ cycloalkyl, —$C_0$-$C_4$ alkyl-Ar, —$C_0$-$C_4$ alkyl-Het and —$C_0$-$C_4$ alkyl-$C_3$-$C_7$ cycloalkyl, where x is 0, 1 or 2, or $R^{14}$ and $R^{15}$, together with the nitrogen to which they are attached, form a 4-7 membered heterocyclic ring which optionally contains one or more additional heteroatoms selected from N, O, and S, wherein said $C_1$-$C_6$ alkyl, $C_3$-$C_6$ alkenyl, $C_3$-$C_6$ alkynyl are optionally substituted by one or more of the substituents independently selected from the group halo, —OH, —SH, —$NH_2$, —NH(unsubstituted $C_1$-$C_4$ alkyl), —N(unsubstituted $C_1$-$C_4$ alkyl)(unsubstituted $C_1$-$C_4$ alkyl), unsubstituted —O$C_1$-$C_4$ alkyl, —$CO_2$H, —$CO_2$(unsubstituted $C_1$-$C_4$ alkyl), —$CONH_2$, —CONH(unsubstituted $C_1$-$C_4$ alkyl), —CON(unsubstituted $C_1$-$C_4$ alkyl)(unsubstituted $C_1$-$C_4$ alkyl), —$SO_3$H, —$SO_2NH_2$, —$SO_2$NH(unsubstituted $C_1$-$C_4$ alkyl) and —$SO_2$N(unsubstituted $C_1$-$C_4$ alkyl)(unsubstituted $C_1$-$C_4$ alkyl);

or a pharmaceutically acceptable salt or solvate thereof.

Unless otherwise provided, each alkyl, alkoxy, alkenyl, alkynyl, cycloalkyl, aryl or Het herein is independently unsubstituted or substituted with one ore more substituents defined hereinabove.

The LXR modulating agents of this invention may contain the variety of U groups defined above. In one embodiment of this invention, U is selected from halo, —$OR^{10}$, —$NR^{11}R^{12}$, cyano, —$COOR^{10}$, —$OCOR^{13}$, —$SO_2NR^{14}R^{15}$, —C(=$NR^{17}$)$NR^{14}R^{15}$, —N($R^{14}$)$COR^{16}$ and a 5 or 6-membered heterocyclic group. In another embodiment, U is selected from halo, $OR^{10}$, —$COOR^{10}$, —$CONR^{11}R^{12}$, —$SO_2NR^{11}R^{12}$, —C(=NH)$NR^{11}R^{12}$, and a 5 or 6-membered heterocyclic group. In other embodiments, U is halo, —$OR^{10}$, —$COOR^{10}$, —$CONR^{11}R^{12}$, —$NR^{11}R^{12}$, or a 5 or 6-membered heterocyclic group more specifically, U is —$OR^{10}$, —$COOR^{10}$, —$CONR^{11}R^{12}$ or —$NR^{11}R^{12}$. For example, U may be selected from bromo, —OH, —COOH, —$COOCH_3$, —$CONH_2$, —$COOCH_3$, —CON(H)$CH_2$-furan-2-yl, —N(H)$CH_2$-furan-2-yl,triazolyl triazolyl and tetrazolyl. In specific embodiments of the compounds of this invention, U is —OH, —COOH, —$CONH_2$, —CON(H)$CH_2$-furan-2-yl, or —N(H)$CH_2$-furan-2-yl.

In specific embodiments, the compounds of this invention are defined wherein p is 0-3. In preferred embodiments, p is 0, 1 or 2. In specific embodiments of this invention, p is 1 or 2.

In other embodiments, each $R^1$ and $R^2$ are independently selected from H, $C_1$-$C_4$ alkyl and —$C_0$-$C_4$ alkyl-$OR^{11}$. By virtue of the definitions given above for the term "alkyl", this definition of $R^3$ also encompasses alkyl groups that are optionally substituted with the substituents specified in the definitions above. Accordingly, in the compounds and methods of this invention, each $R^1$ and $R^2$ may be independently selected from H, $C_1$-$C_4$ alkyl, —OH, —$C_1$-$C_4$ alkyl-OH, —$C_1$-$C_4$ alkyl-$NH_2$, —$C_1$-$C_4$ alkyl-NH($C_1$-$C_4$ alkyl), and —$C_1$-$C_4$ alkyl-N($C_1$-$C_4$ alkyl)($C_1$-$C_4$ alkyl). In a specific embodiment of the compounds of this invention, $R^1$ and $R^2$ are H.

The group

describes a 6-membered aromatic ring, specifically, a phenyl or pyridyl ring, which may be unsubstituted (k=0) or substituted by one or more substituents $R^3$. In a preferred embodiment, the compounds of this invention are defined where the A group is a phenyl fused ring moiety. The total number of $R^3$ substituents that may be present in a compound of this invention is represented by "k". When A is a phenyl fused ring moiety, k is 0-3, meaning that there can be up to three $R^3$ substituents on the 6-membered aromatic ring. When A is a pyridyl fused ring moiety, k is 0-2, meaning that there can be up to two $R^3$ substituents on the 6-membered aromatic ring. In this embodiment, $R^3$ is not attached to the N atom of the pyridyl ring moiety ring. Preferably, k is 0 or 1. In specific embodiments, k is 0.

In the embodiments wherein k is 1 or more, each $R^3$ may be the same or different and may be independently selected from halo, $C_1$-$C_4$ alkyl and $C_1$-$C_4$ alkoxy. By virtue of the definitions given above for the term "alkyl", this definition of $R^3$ also encompasses alkyl groups that are optionally substituted with the substituents specified in the definitions above.

When the moiety —Y(CR$^4$R$^5$)$_n$— is substituted and $R^4$ and $R^5$ are different on at least one (CR$^4$R$^5$) moiety (e.g., when one of $R^4$ or $R^5$ is methyl and the other of $R^4$ and $R^5$ is hydrogen) a chiral compound is obtained. All single stereoisomers, mixtures and racemates of these chiral compounds are intended to be encompassed within the broad scope of the present invention.

In another embodiment, the compounds of this invention of this invention are defined wherein n is 2-4. In specific embodiments, n is 2.

In the compounds of this invention, t may be 0 or 1. When t is 1, the compound of this invention is the N-oxide of the tertiary amine, having the formula:

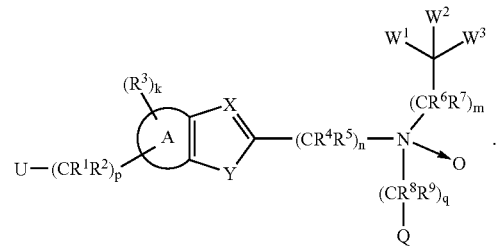

When t is 0, the compound of this invention is the tertiary amine having the formula:

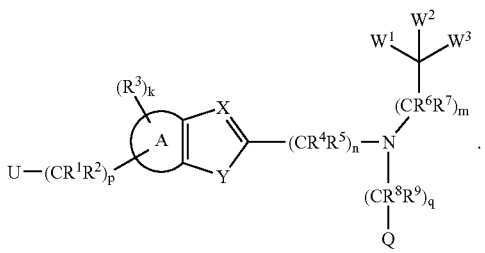

In specific embodiments of the compounds this invention, q is 1 and $R^8$ and $R^9$ are both H.

Group Q is selected from $C_3$-$C_7$ cycloalkyl, aryl and Het. By virtue of the definitions given above for the terms "cycloalkyl", "aryl" and "Het", this definition of Q also encompasses cycloalkyl, aryl and Het groups that are optionally substituted from 1 to 4 times, more preferably, from 1 to 3 times. In one embodiment, Q is an aryl group or a Het group. In specific non-limiting embodiments, Q is a substituted phenyl group, containing one or two substituents selected from halo, $C_1$-$C_4$ alkoxy; and $C_1$-$C_4$ alkyl (specifically including $C_1$-$C_4$ haloalkyl) or Q is a 1,3-benzodioxolyl or dihydrobenzofuranyl group. More specifically, Q is a phenyl group substituted by one or two substituents selected from chloro, trifluoromethyl and methoxy or is a 1,3-benzodioxolyl or a dihydrobenzofuranyl group. Specifically, in the compounds of this invention, Q is 2-chloro-3-trifluoromethylphenyl, 4-methoxyphenyl, 2,4-dimethoxyphenyl, benzo[1,3]dioxol-5-yl, or (2,3-dihydro)benzofuran-5-yl.

In one embodiment of the compounds of this invention, m is 0 or 1 and $R^6$ and $R^7$ are independently selected from H and $C_1$-$C_4$ alkyl. In another embodiment, $W^3$ is H. In yet another embodiment, $W^1$ and $W^2$ are the same or different and are selected from $C_3$-$C_6$ cycloalkyl, aryl and Het. In another embodiment, m is 1, $R^6$ and $R^7$ are both H, $W^3$ is H, $W^1$ is selected from $C_3$-$C_6$ cycloalkyl, aryl and Het and $W^2$ is selected from $—CO_2R^{10}$, $—NR^{11}R^{12}$, $—CONR^{11}R^{12}$, $—OCOR^{13}$, $—OCONR^{11}R^{12}$, $C_1$-$C_4$ alkyl, $—C_0$-$C_4$ alkyl-$OR^{10}$, $—C_1$-$C_4$ alkyl-Het, $—C_1$-$C_4$ alkyl-Ar and $—C_1$-$C_4$ alkyl-$C_3$-$C_6$ cycloalkyl. In other embodiments of the compounds of this invention, m is 0 or m is 1 and $R^6$ and $R^7$ are both H, $W^1$ is selected from $C_3$-$C_6$ cycloalkyl, aryl and Het and $W^2$ and $W^3$ are each H. By virtue of the definitions given above, for the terms "alkyl", "cycloalkyl", "aryl" and "Het", $W^1$ and $W^2$ also encompasses the foregoing groups optionally substituted with the substituents specified in the definitions above. In one embodiment, $W^1$ and/or $W^2$ may be phenyl, thienyl, pyridyl, furanyl, pyrrolyl, morpholinyl, or pyrrolidinyl, where each phenyl, thienyl, pyridyl, furanyl, pyrrolyl, morpholinyl, or pyrrolidinyl may be optionally substituted from 1 to 3 times, more preferably from 1 to 2 times with one or more of the substituents defined hereinabove. For example, $W^1$ and/or $W^2$ may be independently substituted by one or more substituents independently selected from $C_1$-$C_4$ alkyl, —OH, halo, —O—$C_1$-$C_4$ alkyl, and —$C_1$-$C_4$ haloalkyl. In another embodiment, $W^1$ may be phenyl, thienyl, pyridyl, furanyl, pyrrolyl, morpholinyl, or pyrrolidinyl and $W^2$ may be phenyl, thienyl, pyridyl, furanyl, pyrrolyl, morpholinyl, pyrrolidinyl, cyclohexyl, cyclopentyl, $C_1$-$C_4$ alkyl (such as methyl, ethyl, n-propyl, isopropyl, n-butyl, iso-butyl, tert-butyl and secbutyl) or $C_1$-$C_4$ haloalkyl, where each phenyl, thienyl, pyridyl, furanyl, pyrrolyl, morpholinyl, or pyrrolidinyl may be optionally independently substituted with 1, 2 or 3 substituents independently selected from $C_1$-$C_4$ alkyl, —OH, halo, —O—$C_1$-$C_4$ alkyl, and —$C_1$-$C_4$ haloalkyl.

In specific embodiments of this invention, m is 1 and $R^6$ and $R^7$ are both H, $W^1$ is aryl and $W^2$ is aryl or $C_1$-$C_4$ alkyl. In more specific embodiments, m is 1 and $R^6$ and $R^7$ are both H, $W^3$ is H, $W^1$ and $W^2$ are each unsubstituted phenyl or $W^1$ is unsubstituted phenyl and $W^2$ is methyl.

In other embodiments of this invention, the $—C_0$-$C_6$ alkyl- and $—C_0$-$C_4$ alkyl-moieties of the substitutents defined herein are unsubstituted $—C_0$-$C_6$ alkyl- and unsubstituted $—C_0$-$C_4$ alkyl- moieties, respectively.

It is to be understood that the present invention covers all combinations of particular and preferred groups described hereinabove.

Specific embodiments of this invention comprise compounds of Formula I and Formula II wherein $R^1$, $R^2$, $R^3$, $R^4$, $R^5$, $R^6$, $R^7$, $R^8$ and $R^9$ are each H; U is $—OR^{10}$, $—COOR^{10}$, $—CONR^{11}R^{12}$ or $—NR^{11}R^{12}$; A is a phenyl fused ring; Q is a substituted phenyl group containing one or two substituents selected from halo, $C_1$-$C_4$ alkoxy and $C_1$-$C_4$ alkyl or Q is a 1,3-benzodioxolyl or a dihydrobenzofuranyl group; p is 1 or 2; n is 2; m is 1; q is 1; k is 0; t is 0; $W^1$ is aryl; $W^2$ is aryl or $C_1$-$C_4$ alkyl; and $W^3$ is H; or a pharmaceutically acceptable salt or solvate thereof.

More specific embodiments of this invention comprise compounds of Formula I and Formula II wherein $R^1$, $R^2$, $R^3$, $R^4$, $R^5$, $R^6$, $R^7$, $R^8$, $R^9$ and $W^3$ are each H; U is —OH, —COOH, $—CONH_2$, $—CON(H)CH_2$-furan-2-yl, or $—N(H)CH_2$-furan-2-yl; A is a phenyl fused ring; Q is a phenyl group substituted by one or two substituents selected from chloro, trifluoromethyl and methoxy or Q is a 1,3-benzodioxolyl or a dihydrobenzofuranyl group; p is 1 or 2; n is 2; m is 1; q is 1; k is 0; t is 0; $W^1$ is unsubstituted phenyl; and $W^2$ is methyl or unsubstituted phenyl; or a pharmaceutically acceptable salt or solvate thereof.

Compounds of this invention include:

2-[2-{[2-chloro-3(trifluoromethyl)-benzyl](2,2-diphenylethyl)amino}ethyl]-5-benzofuran acetic acid, 2-[2-{[2,4-dimethoxy-benzyl](2,2-diphenylethyl) amino}ethyl]-5-benzofuran acetic acid, 2-[2-{[(2,3-methylenedioxy)benzyl](2,2-diphenylethyl) amino}ethyl]-5-benzofuran acetic acid, 2-[2-{[(2,3-dihydrobenzo[b]furan)methyl](2,2-diphenylethyl)amino}ethyl]-5-benzofuran acetic acid, 2-[2-{[4-methoxy-benzyl](2,2-diphenylethyl) amino}ethyl]-5-benzofuran acetic acid, (R)-2-[2-{[2-chloro-3-(trifluoromethyl)-benzyl](2-methyl-2-phenylethyl)amino}ethyl]-5-benzofuran acetic acid, (R)-2-[2-{[(2,3-dihydrobenzo[b]furan)methyl](2-methyl-2-phenylethyl)amino}ethyl]-5-benzofuran acetic acid, (S)-2-[2-[{[2-chloro-3-(trifluoromethyl)-benzyl](2-methyl-2-phenylethyl)amino}ethyl]-benzofuran acetic acid, (S)-2-[-{2[(2,3-dihydrobenzo[b]furan)methyl](2-methyl-2-phenylethyl)amino}ethyl]-5-benzofuran acetic acid, 2-{2-[[2-chloro-3-(trifluoromethyl)benzyl](2,2-diphenylethyl)amino]-ethyl}-6-benzofuran acetic acid, 2-[2-{[(2,3-methylenedioxy)benzyl](2,2-diphenylethyl) amino}ethyl]-6-benzofuran acetic acid, 2-[2-{[(2,4-dimethoxy)benzyl](2,2-diphenylethyl) amino}ethyl]-6-benzofuran acetic acid, 2-{2-[(4-methoxy-benzyl)(2,2-diphenylethyl)amino]-ethyl}-6-benzofuran acetic acid, 2-{2-[(2-chloro-3-(trifluoromethyl)-benzyl)-(2,2-diphenylethyl-amino]ethyl}-benzofuran-6-yl)-N-furan-2-yl methyl-acetamide, 2-{2-[(2,4-dimethoxy-benzyl)(2,2-diphenylethyl)-amino] ethyl}-benzofuran-6-yl)-N-furan-2-yl methyl-acetamide, 2-{2-[(2(chloro-3-(trifluoromethyl)-benzyl)(2,2-diphenylethyl-amino]ethyl}-benzofuran-6-yl)-acetamide,
(racemic) 2-{3-[(2-chloro-3-(trifluoromethyl)-benzyl)-(2-phenyl-propyl)-amino]-propyl}-benzofuran-6-yl)-acetic acid,
2-(2-{3-[(2-chloro-3-(trifluoromethyl)-benzyl-(2,2-diphenylethyl)-amino]-propyl}-benzofuran-6-yl)-ethanol,
2-(2-{3-[(2,4-dimethoxy)-benzyl-(2,2-diphenylethyl)-amino]-propyl}-benzofuran-6-yl)-ethanol,
2-{3-[(2-chloro-3-(trifluoromethyl)-benzyl)-((R)-2-phenyl-propyl)-amino]-propyl}-benzofuran-6-yl)-acetic acid,
2-{3-[(2-chloro-3-(trifluoromethyl)-benzyl)-((S)-2-phenyl-propyl)-amino]-propyl}-benzofuran-6-yl)-acetic acid,
(2-chloro-3-trifluoromethyl-benzyl)-(2,2-diphenylethyl)-[3-(6-{2-[(furan-2-ylmethyl)-amino]-ethyl-benzofuran-2-yl)-propyl]-amine,
and a stereoisomer, a stereoisomeric mixture or racemate thereof and a pharmaceutically acceptable salt or solvate thereof.

Preferred compounds of this invention include:
2-[2-{[2,4-dimethoxy-benzyl](2,2-diphenylethyl)amino}ethyl]-5-benzofuran acetic acid,
(R)-2-[2-{[(2,3-dihydrobenzo[b]furan)methyl](2-methyl-2-phenylethyl)amino}ethyl]-5-benzofuran acetic acid,
2-{2-[[2-chloro-3-(trifluoromethyl)benzyl](2,2-diphenyl-ethyl)amino]-ethyl}-6-benzofuran acetic acid,
2-[2-{[(2,4dimethoxy)benzyl](2,2-diphenylethyl)amino}ethyl]-6-benzofuran acetic acid,
and a stereoisomer, a stereoisomeric mixture or racemate thereof and a pharmaceutically acceptable salt or solvate thereof.

As used herein, the term "LXR agonist" refers to compounds which achieve at least 20% activation of LXR relative to 24(S),25-epoxycholesterol, the appropriate positive control in the HTRF assay described below in Test Method 1. It should be noted that to show activity in the specific Test Methods described herein, the LXR modulator compound must bind to the LXR nuclear receptor and recruit the specific peptide derived from the coactivator protein, SRC1, to the modulator compound-bound LXR complex. The compounds of this invention that form an LXR-modulator compound complex and recruit SRC1, may also recruit at least one or more of the other >80 known different nuclear receptor cofactors. Recruiter peptides derived from any of these other nuclear receptor cofactors may be similarly prepared and assayed according to known procedures.

The compounds of this invention are useful for a variety of medicinal purposes. The compounds of this invention may be used in methods for the prevention or treatment of LXR mediated diseases and conditions. This invention further provides compounds of this invention for use in the preparation of a medicament for the prevention or treatment of an LXR mediated disease or condition. LXR mediated diseases or conditions include inflammation, cardiovascular disease including atherosclerosis, arteriosclerosis, hypercholesteremia, and hyperlipidemia. In particular, the compounds of this invention are useful in the treatment and prevention of inflammation, cardiovascular disease including atherosclerosis and hypercholesteremia.

The present invention also provides a method for increasing reverse cholesterol transport, compounds of this invention for increasing reverse cholesterol transport and the use of compounds of this invention for the preparation of a medicament for increasing reverse cholesterol transport. Lipoprotein metabolism is a dynamic process comprised of production of triglyceride rich particles from the liver (as VLDL), modification of these lipoprotein particles within the plasma (VLDL to IDL to LDL) and clearance of the particles from the plasma, again by the liver. This process provides the transport of triglycerides and free cholesterol to cells of the body. Reverse cholesterol transport is the proposed mechanism by which peripheral cholesterol is returned to the liver from extra-hepatic tissue. The process is carried out by HDL cholesterol. The combination of lipoprotein production (VLDL, HDL) from the liver, modification of particles (all) within the plasma and subsequent clearance back to the liver, accounts for the steady state cholesterol concentration of the plasma. Without wishing to be bound by any particular theory, it is currently believed that the compounds of this invention increase reverse cholesterol transport by increasing cholesterol efflux from the arteries.

Additionally, this invention provides a method for inhibiting cholesterol absorption, compounds of this invention for inhibiting cholesterol absorption and the use of compounds of this invention for the preparation of a medicament for inhibiting cholesterol absorption. This invention also provides a method for increasing reverse cholesterol transport, compounds of this invention for increasing reverse cholesterol transport and the use of compounds of this invention for the preparation of a medicament for increasing reverse cholesterol transport.

The compounds of this invention may also be useful for the prevention or treatment of inflammation and neurodegenerative diseases or neurological disorders. Accordingly, this invention also provides a method for preventing or treating inflammation (See A. J. Fowler et al., J. Invest. Dermatol., 2003 February, 120 (2): 246-255 and S. B. Joseph, et al. Nat. Med., Feb. 9, 2003 (2): 213-219) and a method for preventing or treating neurodegenerative diseases or neurological disorders, particularly neurodegenerative diseases or disorders characterized by neuron degeneration, neuron injury or impaired plasticity or inflammation in the CNS (as disclosed in U.S. Provisional Patent Application Ser. No. 60/368,424, filed 27 March, 2002). Particular diseases or conditions that are characterized by neuron degeneration and inflammation, and thus benefiting from the growth and/or repair of neurons include stroke, Alzheimer's disease, fronto-temporal dementias (tauopathies), peripheral neuropathy, Parkinson's disease, dementia with Lewy bodies, Huntington's disease, amyotrophic lateral sclerosis and multiple sclerosis. Diseases or conditions that are characterized by neuron degeneration and/or impaired plasticity include psychiatric disorders such as schizophrenia and depression. Particular diseases or conditions that are characterized by neuronal injury include those conditions associated with brain and/or spinal cord injury, including trauma.

The methods of the present invention are useful for the treatment of animals including mammals generally and particularly humans. The present invention further provides the use of compounds of this invention for the preparation of a medicament for increasing reverse cholesterol transport.

The methods of the present invention comprise the step of administering a therapeutically effective amount of the compound of this invention. As used herein, the term "therapeutically effective amount" refers to an amount of the compound of this invention that is sufficient to achieve the stated effect. Accordingly, a therapeutically effective amount of a compound of this invention used in the method for the prevention or treatment of LXR mediated diseases or conditions will be an amount sufficient to prevent or treat the LXR mediated disease or condition. Similarly, a therapeutically effective amount of a compound of this invention for use in the method of increasing reverse cholesterol transport will be an amount sufficient to increase reverse cholesterol transport.

The amount of a compound of this invention or pharmaceutically acceptable salt or solvate thereof, which is required to achieve the desired biological effect will depend on a number of factors such as the use for which it is intended, the means of administration, and the recipient, and will be ultimately at the discretion of the attendant physician or veterinarian. In general, a typical daily dose for the treatment of LXR mediated diseases and conditions in a human, for instance, may be expected to lie in the range of from about 0.01 mg/kg to about 100 mg/kg. This dose may be administered as a single unit dose or as several separate unit doses or as a continuous infusion. Similar dosages would be applicable for the treatment of other diseases, conditions and therapies including increasing reverse cholesterol transport, and inhibiting cholesterol absorption.

In another embodiment, the present invention provides pharmaceutical compositions comprising a compound of this invention or a pharmaceutically acceptable salt or solvate thereof, as the active ingredient, and at least one pharmaceutical carrier or diluent. These pharmaceutical compositions may be used in the prophylaxis and treatment of the foregoing diseases or conditions and in cardiovascular therapies as mentioned above. The carrier must be pharmaceutically acceptable and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredient.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the disease or condition being treated or the nature of the therapy being used and on the nature of the active compound, but where possible, oral administration is preferred for the prevention and treatment of LXR mediated diseases and conditions.

Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically a flavored base, such as sugar and acacia or tragacanth and pastiles comprising the active compound in an inert base, such as gelatin and glycerine or sucrose acacia.

Formulations suitable for parenteral administration typically comprise sterile aqueous solutions containing a predetermined concentration of the active compound; the solution is preferably isotonic with the blood of the intended recipient. Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions are preferably administered intravenously, they may also be administered by subcutaneous or intramuscular injection.

Formulations suitable for rectal administration are preferably provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by molding an intimate mixture of powdered active ingredient and inert liquid diluent.

Suitable formulations for administration by inhalation include fine particle dusts or mists which may be generated by means of various types of metered dose pressurized aerosols, nebulisers, or insufflators.

For pulmonary administration via the mouth, the particle size of the powder or droplets is typically in the range 0.5-10 μM, preferably 1-5 μM, to ensure delivery into the bronchial tree. For nasal administration, a particle size in the range 10-500 μM is preferred to ensure retention in the nasal cavity.

Metered dose inhalers are pressurized aerosol dispensers, typically containing a susperision or solution formulation of the active ingredient in a liquefied propellant. During use, these devices discharge the formulation through a valve adapted to deliver a metered volume, typically from 10 to 150 μL, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol surfactants, such as oleic acid or sorbitan trioleate, anti-oxidants and suitable flavoring agents. Nebulisers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulisers consist of the active ingredient in a liquid carrier and comprising up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavoring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

In addition to the ingredients specifically mentioned above, the formulations of the present invention may include other agents known to those skilled in the art of pharmacy, having regard for the type of formulation in issue. For example, formulations suitable for oral administration may include flavoring agents and formulations suitable for intra-nasal administration may include perfumes.

General Methods

In one embodiment of this invention, the method for the preparation of compounds of Formulas I or II comprises the steps of:

(a) coupling an acetylene having the formula: with a phenol having the formula:

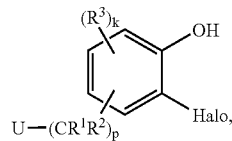

where Halo is a halogen selected from iodo and bromo, in the presence of a metal catalyst to form an aryl-alcohol having the formula:

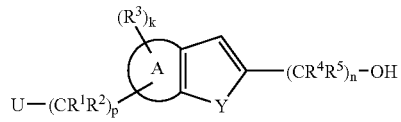

(b) converting alcohol moiety of the aryl-alcohol formed in step (a) into L', where L' is a leaving group such as a halogen (iodide, bromide or chloride), sulfonate (tosylate, mesylate, triflate, etc.) or is a group that is converted to a leaving group (e.g., an alcohol), and treating the resulting compound with an amine having the formula:

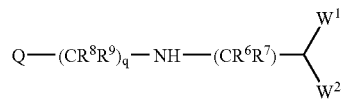

to form the compound of Formula I or Formula II, respectively;

(c) optionally converting the compound of Formula I or Formula II from step (b) into another compound of Formula I or Formula II, respectively; and (d) optionally oxidizing the compound formed in step (c) to the N-oxide thereof.

In another embodiment of this invention, the method for the preparation of compounds of Formulas I or II comprises the steps of:

(a) coupling an acetylene having the formula: with a phenol having the formula:

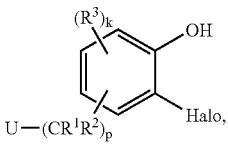

where Halo is a halogen selected from iodo and bromo, in the presence of a metal catalyst to form an aryl-alcohol having the formula:

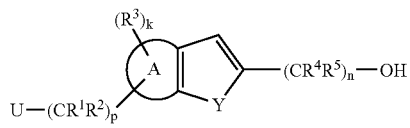

(b) converting alcohol moiety of the aryl-alcohol formed in step (a) into L', where L' is a leaving group such as a halogen (iodide, bromide or chloride) or a sulfonate (tosylate, mesylate, triflate, etc.) and treating the resulting compound with sodium azide, followed by hydrogenation in the presence of a palladium catalyst to form a primary amine having the formula:

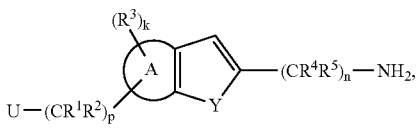

(c) treating the primary amine with a first aldehyde in the presence of a reducing agent, to form a secondary amine and treating the secondary amine with a second aldehyde in the presence of a reducing agent to form the compound of Formula I or Formula II, respectively,

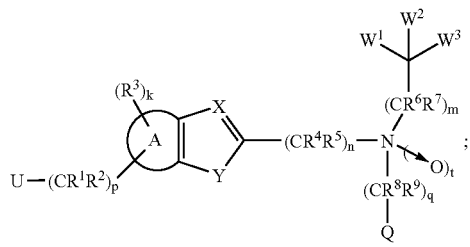

(d) optionally converting the compound of Formula I or Formula II from step (b) into another compound of Formula I or Formula II, respectively; and (e) optionally oxidizing the compound formed in step (b) or (c) to the N-oxide thereof.

Specific Methods

Compounds of Formula I or Formula II with benzofuran substitution at the 6-position were prepared by methods analogous to those described in Scheme 1.

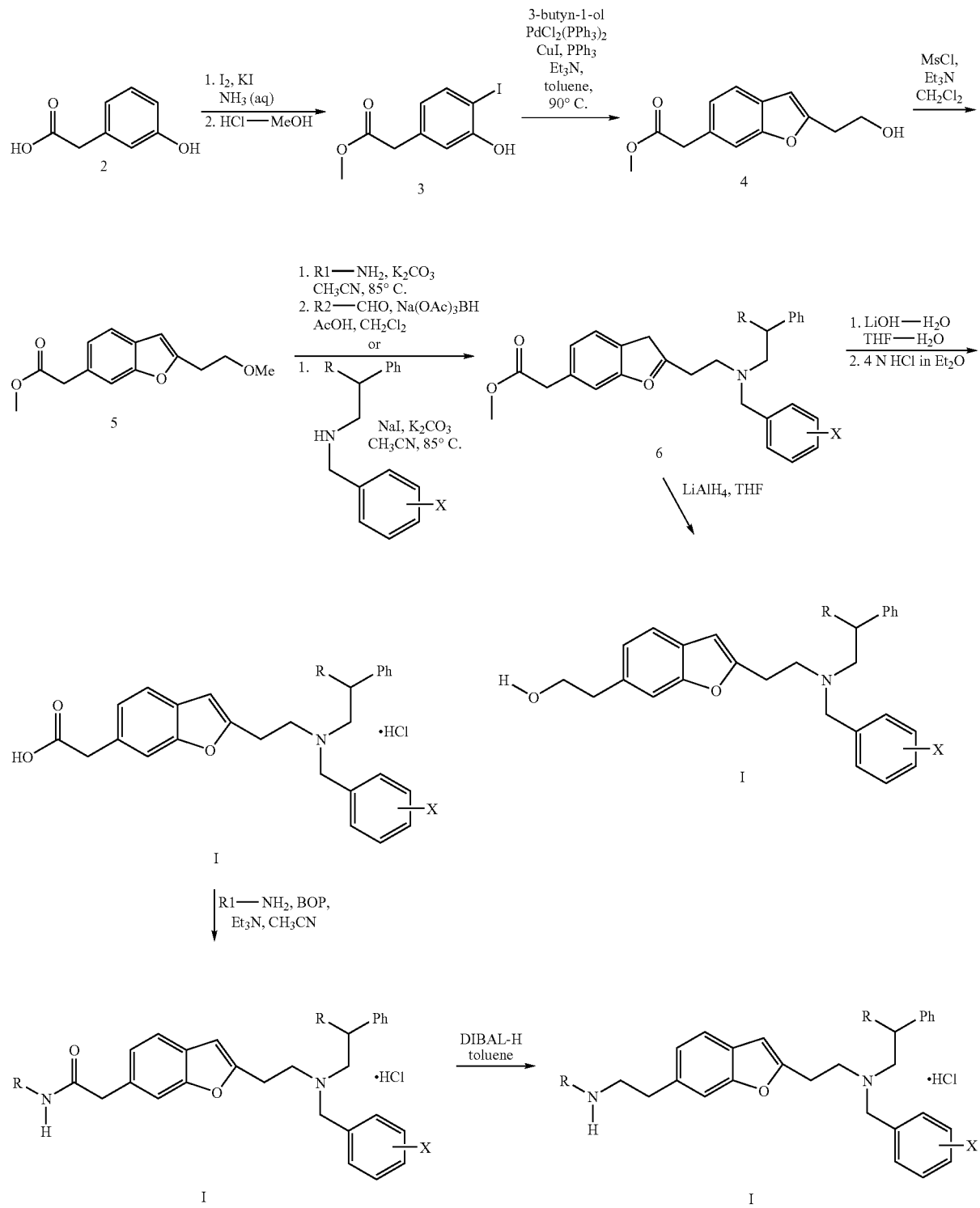
Scheme 1

Scheme 2

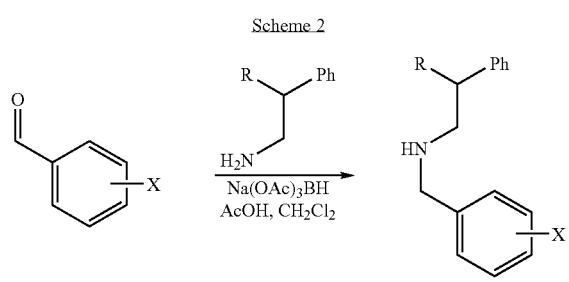

The phenol 1 was iodinated using triiodoamine (generated in situ) to provide the corresponding phenylacetic acid as indicated in Scheme 1. The acid was converted to the methyl ester under standard esterification conditions. Treatment of the methyl ester with PdCl$_2$(PPh$_3$)$_2$ in the presence of CuI led the formation of benzofuran 3. The benzofuran was converted to the mesylate 5. Mesylate 5 was either alkylated directly with a secondary amine (such as N-(2,2-diphenylethyl)-N-(4-methoxy-benzyl)amine—prepared in Scheme 2) to form 6, or alkylated with a primary amine (such as N-2,2-diphenylethylamine) to form a secondary amine and then reductively aminated using a substituted benzaldehyde (such as 2-chloro-3-trifluoromethylbenzaldehyde, 2,3-methylenedioxy)benzaldehyde, and 2,4-di-methoxy)benzaldehyde) to afford the tertiary amine 6. The methyl ester 6 was then hydrolyzed using lithium hydroxide, and the resulting carboxylic acid was treated with 4 N HCl to form the tertiary amine HCl salt I. The methyl ester 6 may also be converted to the corresponding alcohol I by treatment of the ester with lithium aluminum hydride in THF.

The carboxylic acid/tertiary amine I was converted to the corresponding amide I by using a standard amidation procedure employing BOP, triethylamine, and an appropriate amine (ammonia or furfuryl-amine). The amide I may be converted to the corresponding amine I by treatment of the amide with DIBAL-H in toluene.

Compounds of Formula I or Formula II with benzofuran substitution at the 5-position were prepared by methods analogous to those described in Scheme 2.

Scheme 3

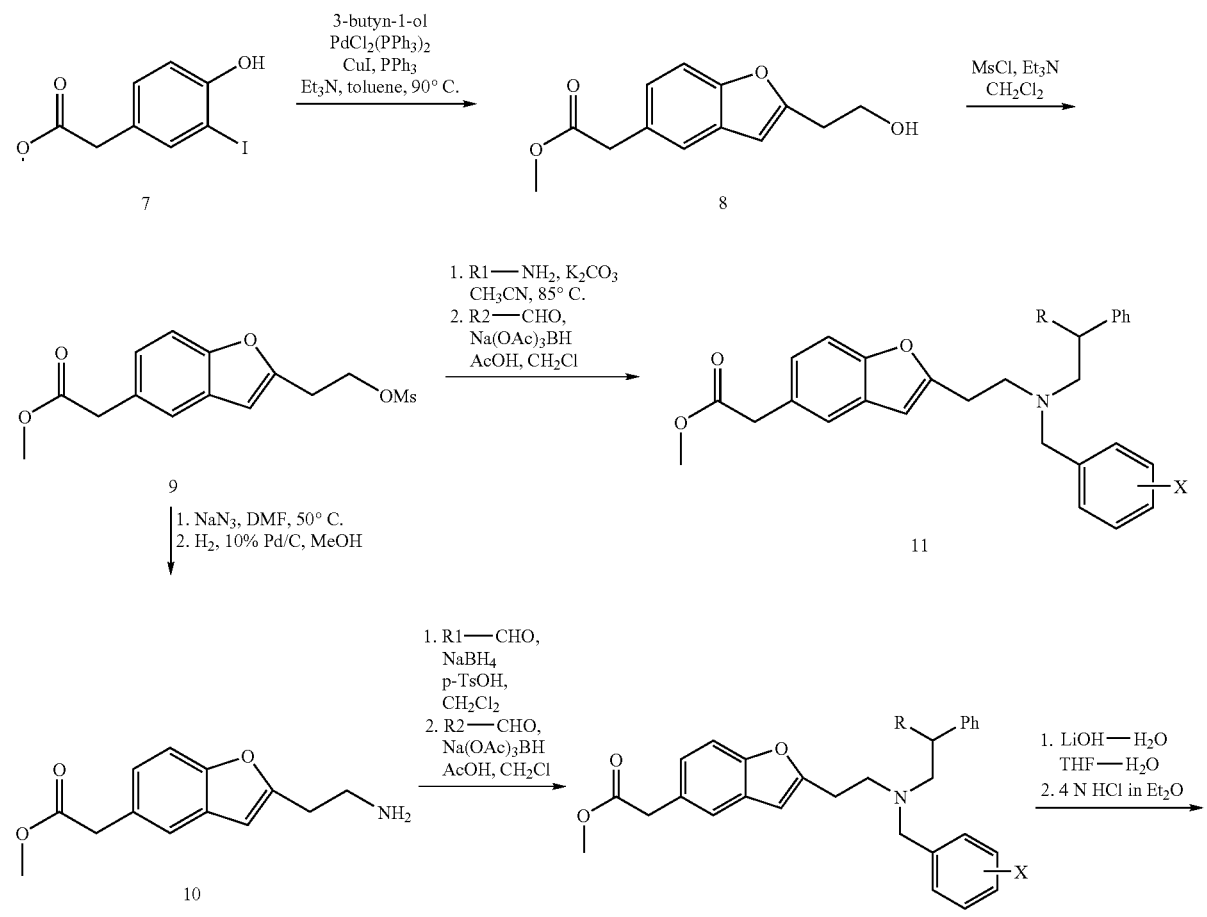

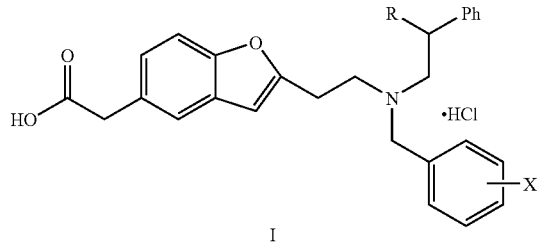

I

Treatment of the methyl ester with PdCl$_2$(PPh$_3$)$_2$ in the presence of CuI led to the formation of benzofuran 8 as illustrated in Scheme 3. The benzofuran was next converted to the mesylate 9. Two synthetic routes were utilized to prepare tertiary amine 11. In the first procedure, the mesylate 9 was alkylated with a primary amine (such as (R)-(+)-□-methylphenylethylamine or (S)-(−)-□-methylphenylethylamine) to form the corresponding secondary amine. The secondary amine was then reductively aminated with a substituted benzaldehyde (such as 2-chloro-3-trifluoromethylbenzaldehyde and 2,3-dihydrobenzo[b]furan-5-carboxaldehyde) to provide the tertiary amine 11. In the second procedure, mesylate 9 was converted to the azide, and then the azide was subjected to a catalytic hydrogenation to afford the primary amine 10. The primary amine 10 was then reductively aminated with diphenylacetaldehyde to form the secondary amine, and the secondary amine was subjected to a second reductive amination with a substituted benzaldehyde (such as 2-chloro-3-trifluoromethylbenzaldehyde, 2,3-methylenedioxy)benzaldehyde, 2,4-di-methoxy)benzaldehyde, 4-methoxybenzaldehyde and 2,3-dihydrobenzo[b]furan-5-carboxaldehyde) to afford 11. The methyl ester 11 was then hydrolyzed using lithium hydroxide, and the resulting carboxylic acid was treated with 4 N HCl to form the tertiary amine HCl salt I.

Each of the above-described methods further include the optional step(s) of forming a pharmaceutically acceptable salt of a compound of this invention, and/or of forming a pharmaceutically acceptable solvate of a compound of this invention or a pharmaceutically acceptable salt thereof.

The following intermediates are useful in the methods described herein to make the compounds of Formulas I and II:

2-[2-[(2,2-diphenylethyl)amino]ethyl]-5-benzofuran acetic acid methyl ester,

2-[2-[[2-chloro-3-(trifluoromethyl)benzyl-(2,2-diphenylethyl)amino]ethyl]-5-benzofuran acetic acid methyl ester, 2-[2-{[2,4-dimethoxy-benzyl](2,2-diphenylethyl)amino}ethyl]-5-benzofuran acetic acid methyl ester, 2-[2-{[(2,3-methylenedioxy)benzyl](2,2-diphenylethyl)amino}ethyl]-5-benzofuran acetic acid methyl ester, 2-[2-{[(2,3-dihydrobenzo[b]furan)methyl](2,2-diphenylethyl)amino}ethyl]-5-benzofuran acetic acid methyl ester, 2-[2-{[4-methoxy-benzyl](2,2-diphenylethyl)amino}ethyl]-5-benzofuran acetic acid methyl ester, (R)-2-[2-[(2-methyl-2-phenylethyl)amino]ethyl]-5-benzofuran acetic acid methyl ester, (R)-2-[2-{[2-chloro-3-(trifluoromethyl)-benzyl](2-methyl-2-phenylethyl)amino}ethyl]-5-benzofuran acetic acid methyl ester, (R)-2-[2-{[(2,3-dihydrobenzo[b]furan)methyl](2-methyl-2-phenylethyl)amino}ethyl]-5-benzofuran acetic acid methyl ester, (S)-2-[2-[(2-methyl-2-phenylethyl)amino]ethyl]-5-benzofuran acetic acid methyl ester, (S)-2-[2-[{[2-chloro-3-(trifluoromethyl)-benzyl](2-methyl-2-phenylethyl)amino}ethyl]-benzofuran acetic acid methyl ester, (S)-2-[2-{[(2,3-dihydrobenzo[b]furan)methyl](2-methyl-2-phenylethyl)amino}ethyl]-5-benzofuran acetic acid methyl ester, 2-{2-[(2,2-diphenylethyl)amino]-ethyl}-6-benzofuran acetic acid methyl ester, 2-{2-[[2-chloro-3-(trifluoromethyl)benzyl](2,2-diphenylethyl)amino]-ethyl}-6-benzofuran acetic acid methyl ester, 2-[2{[(2,3-methylenedioxy)benzyl](2,2-diphenylethyl)amino}ethyl]-6-benzofuran acetic acid methyl ester, 2-[2{[(2,4-dimethoxy)benzyl](2,2-diphenylethyl)amino}ethyl]-6-benzofuran acetic acid methyl ester, 2-{2-[(4-methoxy-benzyl)(2,2-diphenylethyl)amino]-ethyl}-6-benzofuran acetic acid methyl ester or a pharmaceutically acceptable salt or solvate thereof.

The following Test Methods and Examples are intended for illustration only and are not intended to limit the scope of the invention in any way; the present invention being defined by the claims.

In the Test Methods and Examples, the following terms have the designated meaning: "pRSETa" is a known expression vector available from Invitrogen; "IPTG" means isopropyl β-D-thiogalactopyranoside; "PO$_4$" means phosphate; "PBS" means phosphate buffered saline; "TBS" means tris-buffered saline; EDTA means ethylenediamine tetraacetic acid; "DTT" means dithiothreitol; "FAF-BSA" means fatty-acid free bovine serum albumin; "SRC-1" means steroid receptor coactivator 1; "CS" means charcoal stripped; "nM" means nanomolar; "µM" means micromolar; "mM" means millimolar; "pM" means picomolar; "mmol" means millimoles; "g" means grams; "ng" means nanograms; "mg/ml" means milligram per milliliter; "µL" means microliters; and "mL" means milliliter.

Test Method 1: Ligand Sensing Assay (LiSA) for LXRβ Agonist Activity

This assay measures the recruitment of a peptide derived from the coactivator protein, SRC1, to the agonist-bound LXR□. Peptides derived from other nuclear receptor cofactors may be similarly prepared and assayed.

To generate the human LXRβ ligand binding domain suitable for LISA, a modified polyhistidine tag (MKKGH-HHHHHG) (SEQ ID No. 1) was fused in frame to the human LXRβ ligand binding domain (amino acids 185-461 of Genbank accession number U07132) and subcloned into the expression vector pRSETa (Invitrogen) under the control of an IPTG inducible T7 promoter. The human LXRβ ligand binding domain was expressed in E. coli strain BL21 (DE3). Ten-liter fermentation batches were grown in Rich PO$_4$ media with 0.1 mg/mL Ampicillin at 25° C. for 12 hours, cooled to 9 20 C. and held at that temperature for 36 hours to a density of OD600=14. At this cell density, 0.25 mM IPTG was added and induction proceeded for 24 hours at 9° C., to a final OD600=16. Cells were harvested by centrifugation (20 minutes, 3500 g, 4° C.), and concentrated cell slurries were stored in PBS at −80° C.

Typically 25-50 g of cell paste is resuspended in 250-500 mL TBS, pH 8.0 (25 mM Tris, 150 mM NaCl). Cells are lysed by passing 3 times through an APV Rannie MINI-lab homogenizer and cell debris is removed by centrifugation (30 minutes, 20,000 g, 4° C.). The cleared supernatant is filtered through coarse pre-filters, and TBS, pH 8.0, containing 500 mM imidazole is added to obtain a final imidazole concentration of 50 mM. This lysate is loaded onto a column (XK-26, 10 cm) packed with Sepharose [Ni++ charged] Chelation resin (available from Pharmacia) and pre-equilibrated with TBS pH 8.0/50 mM imidazole. After washing to baseline absorbance with equilibration buffer, the column is washed with approximately one column volume of TBS pH-8.0 containing 95 mM imidazole. LXRβLBD (185-461) is eluted with a gradient from 50 to 500 mM imidazole. Column peak fractions are pooled immediately and diluted 5 fold with 25 mM Tris pH 8.0, containing 5% 1,2-propanediol, 0.5 mM EDTA and 5 mM DTT. The diluted protein sample is then loaded onto a column (XK-16, 10 cm) packed with Poros HQ resin (anion exchange). After washing to baseline absorbance with the dilution buffer the protein is eluted with a gradient from 50-500 mM NaCl. Peak fractions are pooled and concentrated using Centriprep 10K (Amicon) filter devices and subjected to size exclusion, using a column (XK-26, 90 cm) packed with Superdex-75 resin (Pharmacia) pre-equilibrated with TBS, pH 8.0, containing 5% 1,2-propanediol, 0.5 mM EDTA and 5 mM DTT.

LXRβ protein was diluted to approximately 10 μM in PBS and five-fold molar excess of NHS-LC-Biotin (Pierce) was added in a minimal volume of PBS. This solution was incubated with gentle mixing for 30 minutes at ambient room temperature. The biotinylation modification reaction was stopped by the addition of 2000× molar excess of Tris-HCl, pH 8. The modified LXRβ protein was dialyzed against 4 buffer changes, each of at least 50 volumes, PBS containing 5 mM DTT, 2 mM EDTA and 2% sucrose. The biotinylated LXRβ protein was subjected to mass spectrometric analysis to reveal the extent of modification by the biotinylation reagent. In general, approximately 95% of the protein had at least a single site of biotinylation; and the overall extent of biotinylation followed a normal distribution of multiple sites, ranging from one to nine.

The biotinylated protein was incubated for 20-25 minutes at a concentration of 5 nM in assay buffer (50 mM NaF, 50 mM MOPS-pH 7.5, 0.1 mg/ml FAF-BSA, 0.05 mM CHAPS, 10 mM DTT) with equimolar amounts of streptavidin-AlloPhycoCyanin (APC, Molecular Probes). At the same time, the biotinylated peptide comprising amino acids 676-700 of SRC-1 (CPSSHSSLTERHKILHRLLQEGSPS-CONH2) (SEQ ID No. 2) at a concentration of 10 nM was incubated in assay buffer with a ½ molar amount of streptavidin-labelled Europium (Wallac) for 20-25 minutes. After the initial incubations are completed, a 20 molar excess of biotin was added to each of the solutions to block the unattached streptavidin reagents. After 20 min at room temp, the solutions were mixed yielding a concentration of 5 nM for the dye-labeled LXR protein and 10 nM for SRC-1 peptide.

49 uL of the protein/peptide mixture was added to each well of an assay plate containing 1 ul of test compound serial diluted in 100% DMSO. The final volume in each well was 0.05 mL, and the concentration in the well for the dye-labeled protein and peptide was 5 nM protein and 10 nM SRC1-peptide. The final test compound concentrations were between 33 pM and 20 uM. The plates were incubated at room temp 2-hours and then counted on a Wallac Victor V fluorescent plate reader.

In this assay 1 μM 24(S), 25-epoxycholesterol gave a reading of 20000 fluorescence units over a background reading of 10000 fluorescence units.

Test Method 2: Ligand Sensing Assay for LXRα Agonist Activity

The assay for LXRα was run according to the procedures of Test Method 1, above using his-tagged LXRα ligand binding domain (amino acids 183-447 of Genbank accession number U22662, with the 14$^{th}$ amino acid corrected to A from R). In this assay 1 μM 24(S),25-epoxycholesterol gave a reading of 20000 fluorescence units over a background reading of 10000 fluorescence units.

EXAMPLE 1

2-[2-{[2-chloro-3-(trifluoromethyl)-benzyl](2,2-diphenylethyl)amino}ethyl]-5-benzofuran acetic acid hydrochloride

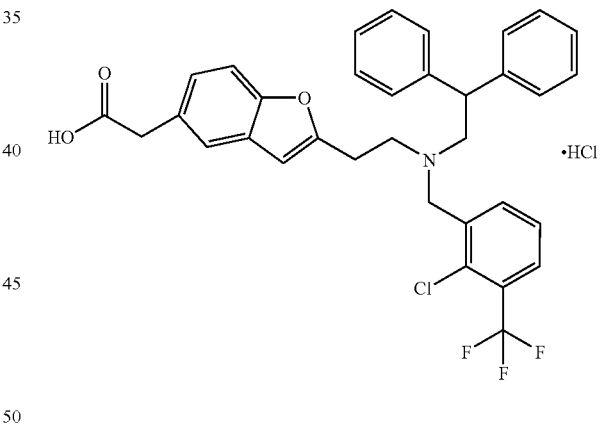

a) 4-Hydroxy-5-iodophenyl acetic acid methyl ester

The title compound was prepared according to the literature procedure (Kometani, T; Watt, D. S., and Ji, T. Tet.Lett. 26 (17), 2043-2046, 1985).

b) 2-(2-hydroxy-ethyl)-5-benzofuran acetic acid methyl ester

To a stirring solution of 4-hydroxy-5-iodophenyl acetic acid methyl ester (1.04 g, 0.0035 mole) and 3-butyn-1-ol (0.5 g, 0.007 mole) in a 3:1 solution of toluene/Et$_3$N (25 mL) was added PPh$_3$ (70 mg, 0.26 mmol), CuI (68 mg, 0.35 mmol), and Pd(PPh$_3$)$_2$Cl$_2$(50 mg, 0.07 mmol). The mixture was heated at 118° C. for 1 h and then cooled to 50° C. To the reaction mixture was added florisil (2 g), the mixture was then stirred for 5 min, cooled to RT, and filtered through a fretted funnel. The crude benzofuran was concentrated and subjected to column chromatography over silica gel (silica gel 60, EM Science) using 1% MeOH:CH$_2$Cl$_2$ as eluent to afford 0.65 g (78% yield) of the title compound as an oil. MS (ESI) 235.0 (M+H$^+$).

c) 2-[2-[(methanesulfonyl)oxy]ethyl]-5-benzofuran acetic acid methyl ester

To a cooled solution (0° C.) of 2-(2-hydroxy-ethyl)-5-benzofuran acetic acid methyl ester (1.5 g, 0.0064 mole) and triethylamine (0.78 g, 0.0077 mole) in dichloromethane (50 mL) was added methanesulfonyl chloride (0.8 g, 0.007 mole). The reaction mixture was warmed to RT and stirred for 1 h. The reaction mixture was poured into H$_2$O, and extracted with CH$_2$Cl$_2$. The organic layer was washed with saturated aqueous NaCl, dried over Na$_2$SO$_4$, and filtered. The filterate was concentrated in vacuo to afford 2.0 g (100% yield) of the compound as an oil. MS (ESI) 313.0 (M+H$^+$).

d) 2-(2-azidoethyl)-5-benzofuran acetic acid methyl ester

To a stirring solution of 2-[2-[(methanesulfonyl)oxy] ethyl]-5-benzofuran acetic acid methyl ester (2.6 g, 8.33 mmol) in DMF (20 mL) was added sodium azide (0.71 g, 0.011 mole). The reaction mixture was heated at 75° C. for 2 h. Additional quantities of DMF (5 mL) and sodium azide (300 mg, 4.6 mmol) were added and the mixture was heated for 2 h. The reaction mixture was cooled to RT, diluted with H$_2$O (40 mL), and extracted three times with EtOAc. The EtOAc extracts were washed with saturated aqueous NaCl, dried over Na$_2$SO$_4$, and filtered. The filtrate was concentrated and the crude product was purified by column chromatography over silica gel (silica gel 60,EM Science) using 10% EtOAc:hexane as eluent to afford 1.8 g (83%) of the title compound as an oil. IR: 2101.74 cm$^{-1}$ (N$_3$). $^1$H-NMR (400 MHz, CDCl$_3$) δ☐7.44-7.38 (m, 2H), 7.18 (m, 1H), 6.51 (s, 1H), 3.72 (s, 3H), 3.62-3.71 (m, 4H), and 3.07 (t, 2H, J=6.8 Hz).

e) 2-[2-[(2,2-diphenylethyl)amino]ethyl]-5-benzofuran acetic acid methyl ester

To a solution of 2-(2-azidoethyl)-5-benzofuran acetic acid methyl ester (1.5 g, 0.006 mole) in MeOH (50 mL) was added 10% palladium on carbon (0.35 g). The mixture was hydrogentated at atmospheric pressure for 0.5 h. The catalyst was filtered using a fritted funnel and the filtrate was concentrated to a volume of 40 mL. The crude primary amine was used without further purification. MS (ESI) 234.0 (M+H$^+$).

To the stirring methanolic solution (above) of 2-(2-aminoethyl)-5-benzofuran acetic acid methyl ester (ca. 6 mmol) was added diphenylacetaldehyde (1.06 g, 0.0054 mole) and a catalytic amount of p-toluenesulfonic acid monohydrate. The reaction mixture was stirred for 45 min. and cooled to 0° C. To the stirring solution was added sodium borohydride (0.3 g, 0.008 mole). The reaction mixture was stirred for 2 h and then concentrated. The resulting residue was dissolved in EtOAc and washed with H$_2$O. The organic layer was washed with saturated aqueous NaCl, dried over Na$_2$SO$_4$, filtered, and concentrated in vacuo. The crude product was purified by column chromatography over silica gel (silica gel 60,EM Science) using 50% EtOAc:hexane to afford 0.5 g (22%) of the title compound as an oil. MS (ESI) 414.2 (M+H$^+$).

f) 2-[2-[[2-chloro-3-(trifluoromethyl)benzyl-(2,2-diphenyl-ethyl)aminol]ethyl]-5-benzofuran acetic acid methyl ester To a stirring solution of 2-[2-[(2,2-diphenylethyl)amino] ethyl]-5-benzofuran acetic acid methyl ester (120 mg, 0.29 mmol) and 2-chloro-3-trifluoromethylbenzaldehyde (60.5 mg, 0.29 mmol) in dichloromethane (2 mL) was added sodium triacetoxyborohydride (68 mg, 0.32 mmol) and 1 drop of glacial acetic acid. The reaction was stirred for 4 h at RT, and then was diluted with EtOAc. The reaction mixture was washed with saturated aqueous NH$_4$Cl, saturated aqueous NaHCO$_3$, and saturated aqueous NaCl. The organic layer was dried over Na$_2$SO$_4$, filtered, and concentrated in vacuo. The crude product was purified by column chromatography over silica gel (Silica gel 60,EM Science) using 10% EtOAc:hexane as eluent to afford the title compound as an oil (0.17 g, 100%). MS (ESI) 606.2 (M+H$^+$).

g) 2-[2-[[2-chloro-3-(trifluoromethyl)benzyl-(2,2-diphenyl-ethyl)amino]ethyl]-5-benzofuran acetic acid hydrochloride To a stirring solution of 2-[2-[[2-chloro-3-(trifluoromethyl)benzyl-(2,2-diphenylethyl)amino]ethyl]-5-benzofuran acetic acid methyl ester (170 mg, 0.28 mmol) in tetrahydrofuran (2.5 mL) and H$_2$O (0.7 mL) was added LiOH H$_2$O (26 mg, 0.616 mmol). The reaction mixture was stirred overnight and then concentrated in vacuo. The resulting residue was diluted with H$_2$O (3 mL) and the aqueous mixture was acidified to pH=1.5 with 1 N HCl (aqueous). The aqueous solution was then extracted three times with EtOAc. The organic layer was washed with H$_2$O and saturated aqueous NaCl. The organic extracts were then dried over Na$_2$SO$_4$, filtered, and concentrated to provide the tertiary amine as an oil. The amine was dissolved in Et$_2$O and acidified with 1.0 N HCl/Et$_2$O. The acidic solution was concentrated in vacuo to afford 74.8 mg (43%) of the title compound as a white solid. MS (ESI) 591.8 (M+H$^+$).

EXAMPLE 2

2-[2-{[2,4-dimethoxy-benzyl](2,2-diphenylethyl)amino}ethyl]-5-benzofuran acetic acid hydrochloride

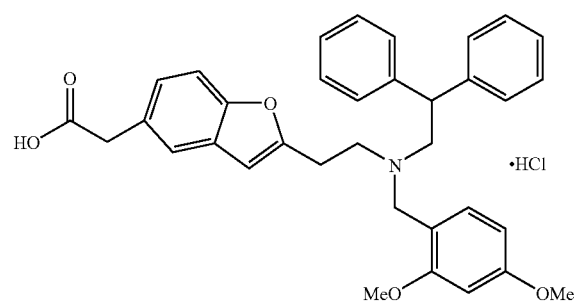

Following the procedure of Example 1(a)-(g) except 2,4-dimethoxybenzaldehyde was used in step 1(f) instead of 2-chloro-3-trifluoromethylbenzaldehyde, the title compound was obtained as a white powder (4% overall). MS (ESI) 550.0 (M+H$^+$).

EXAMPLE 3

2-[2-{[(2,3-Methylenedioxy)benzyl](2,2-diphenyl-ethyl)amino}ethyl]-5-benzofuran acetic acid hydrochloride

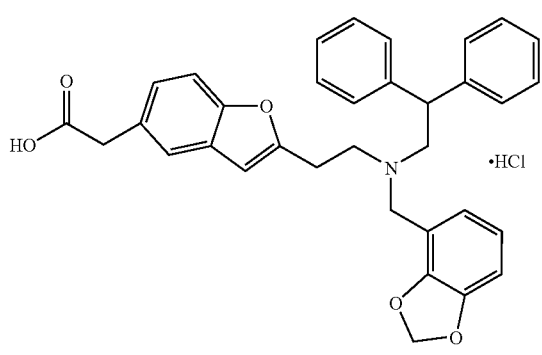

Following the procedure of Example 1(a)-(g) except 2,3-(methylenedioxy)benzaldehyde was used in step 1(f) instead of 2-chloro-3-trifluoromethylbenzaldehyde, the title compound was obtained as a white powder (9% overall). MS (ESI) 534.0 (M+H$^+$).

EXAMPLE 4

2-[2-{[(2,3-dihydrobenzo[b]furan)methyl](2,2-diphenylethyl)amino}ethyl]-5-benzofuran acetic acid hydrochloride

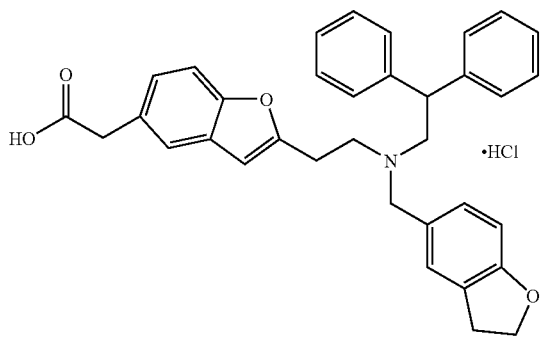

Following the procedure of Example 1(a)-(g) except 2,3-dihydrobenzo[b]furan-5-carboxaldehyde was used in step 1(f) instead of 2-chloro-3-trifluoromethylbenzaldehyde, the title compound was obtained as a white powder (5% overall). MS (ESI) 532.0 (M+H$^+$).

EXAMPLE 5

2-[2-{[4-Methoxy-benzyl](2,2-diphenylethyl)amino}ethyl]-5-benzofuran acetic acid hydrochloride

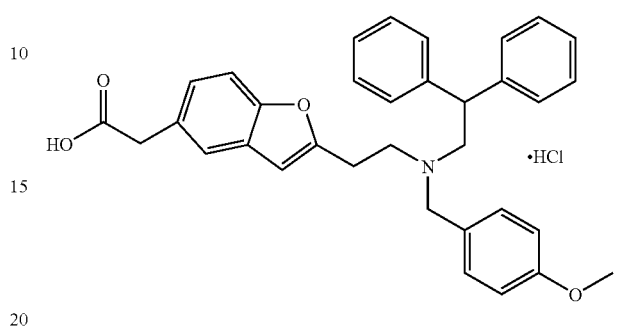

Following the procedure of Example 1(a)-(g) except 4-methoxybenzaldehyde was used in step 1(f) instead of 2-chloro-3-trifluoromethylbenzaldehyde, the title compound was obtained as a white powder (11% overall). MS (ESI) 520.2 (M+H$^+$).

EXAMPLE 6

(R)-2-[2-{[2-chloro-3-(trifluoromethyl)-benzyl](2-methyl-2-phenylethyl)amino}ethyl]-5-benzofuran acetic acid hydrochloride

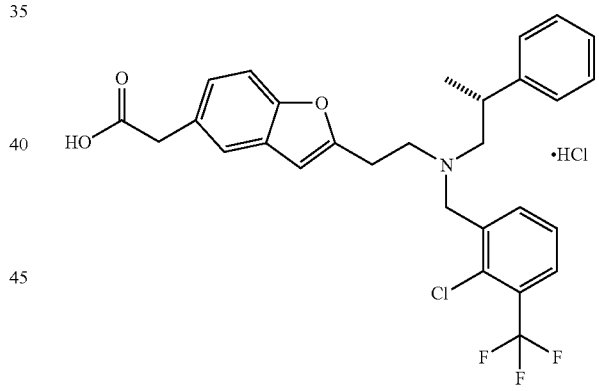

a) (R)-2-[2-[(2-methyl-2-phenylethyl)amino]ethyl]-5-benzofuran acetic acid methyl ester To a stirring solution of 2-[2-[(methanesulfonyl)oxy]ethyl]-5-benzofuran acetic acid methyl ester (100 mg, 0.32 mmol) in CH$_3$CN (10 mL) was added (R)-(+)-β-methylphenylethylamine (44 mg, 0.32 mmol) and K$_2$CO$_3$ (140 mg, 1.0 mmol). The reaction mixture was heated at reflux overnight. The reaction mixture was concentrated in vacuo and the residue was diluted with H$_2$O (10 mL). The aqueous mixture was extracted three times with EtOAc. The organic layer was washed with saturated aqueous NaCl, dried over Na$_2$SO$_4$, and filtered. The filtrate was concentrated and the crude product was purified by column chromatography over silica gel (silica gel 60,EM Science) using 55% EtOAc-hexane to afford 46.8 mg (43%) of the title compound as a white solid. MS (ESI) 352.0 (M+H$^+$).

b) (R)-2-[2-{[2-chloro-3-(trifluoromethyl)-benzyl](2-methyl-2-phenylethyl)amino}ethyl]-5-benzofuran acetic acid methyl ester To a stirring solution of (R)-2-[2-[(2-methyl-2-phenylethyl)amino]ethyl]-5-benzofuran acetic acid methyl ester (73 mg, 0.21 mmol) and 2-chloro-3-trifluoromethylbenzaldehyde (44 mg, 0.21 mmol) in dichloromethane (4 mL) was added sodium triacetoxyborohydride (47 mg, 0.22 mmol) and 1 drop of glacial acetic acid. The reaction mixture was stirred overnight at RT, and was diluted with EtOAc. The reaction mixture was then washed with saturated aqueous NH₄Cl, saturated aqueous NaHCO₃, and saturated aqueous NaCl. The organic layer was dried over Na₂SO₄, and filtered. The filtrate was concentrated and the crude product was purified by column chromatography over silica gel (Silica gel 60, EM Science) using 10% EtOAc:hexane as eluent to afford 73 mg (65%) of the title compound as an oil. MS (ESI) 543.8 (M+H⁺).

c) (R)-2-[2-{2-chloro-3-(trifluoromethyl)-benzyl](2-methyl-2-phenylethyl)amino}ethyl]-5-benzofuran acetic acid hydrochloride To a stirring solution of (R)-2-[2-{[2-chloro-3-(trifluoromethyl)-benzyl](2-methyl-2-phenylethyl)amino}ethyl]-5-benzofuran acetic acid methyl ester (73 mg, 0.13 mmol) in THF (2.5 mL) and H₂O (0.7 mL) was added LiOH H₂O (12 mg, 0.32 mmol). The reaction mixture was stirred overnight and then concentrated in vacuo. The resulting residue was diluted with H₂O (3 mL) and the aqueous mixture was acidified to pH=1.5 with 1 N HCl (aqueous). The aqueous solution was then extracted three times with EtOAc. The organic layer was washed with H₂O and saturated aqueous NaCl. The extracts were then dried over Na₂SO₄, filtered, and concentrated to provide the tertiary amine as an oil. The oil was dissolved in Et₂O and acidified with 1.0 N HCl/Et₂O. The acidic solution was concentrated in vacuo to afford the title compound as a white solid (27.7 mg, 38%). MS (ESI) 530.8 (M+H⁺).

EXAMPLE 7

(R)-2-[2-{[(2,3-dihydrobenzo[b]furan)methyl](2-methyl-2-phenylethyl)amino}ethyl]-5-benzofuran acetic acid hydrochloride

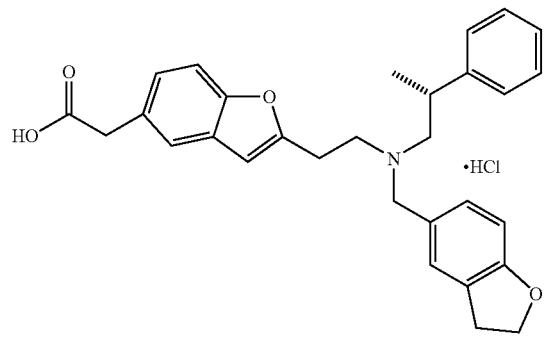

Following the procedure of Example 6(a)-(c) except 2,3-dihydrobenzo[b]furan-5-carboxaldehyde was used in step 6(b) instead of 2-chloro-trifluromethylbenzaldehyde, the title compound was obtained as a white powder (15% overall). MS (ESI) 470.0 (M+H⁺).

EXAMPLE 8

(S)-2-[2-[{[2-Chloro-3-(trifluoromethyl)-benzyl](2-methyl-2-phenylethyl)amino}ethyl]-benzofuran acetic acid hydrochloride

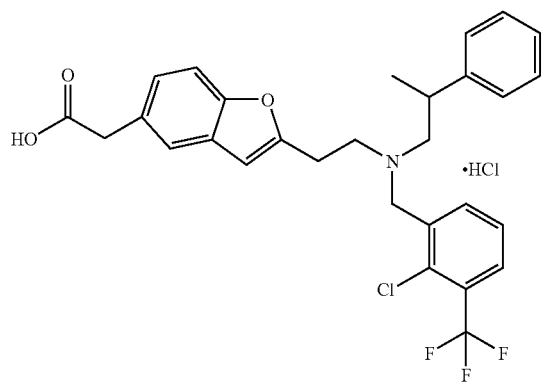

Following the procedure of Example 6(a)-(c) except (S)-(−)-β-methylphenylethylamine was used in step 6(a) instead of (R)-(+)-β-methylphenylethylamine, the title compound was obtained as a white powder (10% overall). MS (ESI) 530.0 (M+H⁺).

EXAMPLE 9

(S)-2-[2-{[(2,3-dihydrobenzo[b]furan)methyl](2-methyl-2-phenylethyl)amino}ethyl]-5-benzofuran acetic acid hydrochloride

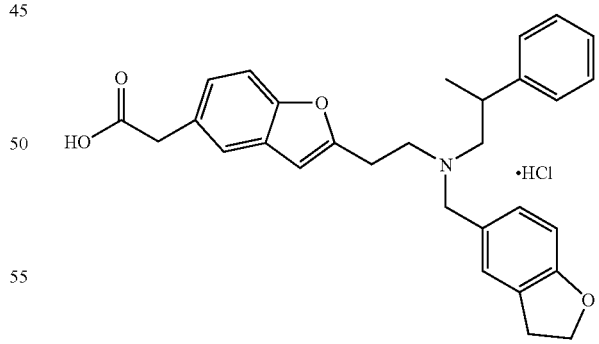

Following the procedure of Example 6(a)-(c) except (S)-(−)-β-methylphenylethylamine was used in step 6(a) instead of (R)-(+)-β-methylphenylethylamine, and in addition, (2,3-dihydrobenzo[b]furan-5-carboxaldehyde was used in step 6(b) instead of 2-chloro-trifluoromethylbenzaldehyde, the title compound was obtained as a white powder (9% overall). MS (ESI) 470.0 (M+H⁺).

EXAMPLE 10

2-{2-[[2-Chloro-3(trifluoromethyl)benzyl](2,2-diphenylethyl)amino]-ethyl}-6-benzofuran acetic acid hydrochloride

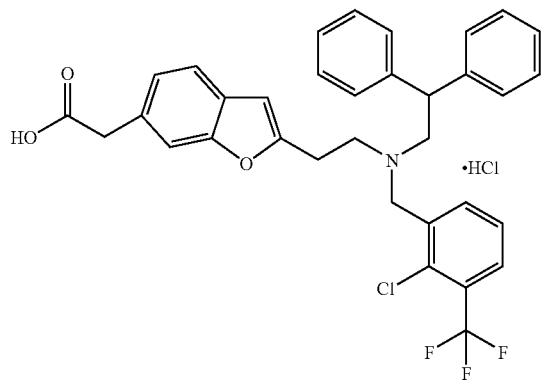

a) (3-hydroxy-4-iodo-phenyl)-acetic acid methyl ester

To a stirring solution of (3-hydroxy-phenyl)-acetic acid (5.0 g, 0.033 mole) in aqueous NH$_2$OH (100 mL NH$_2$OH (aqueous) and 50 mL H$_2$O at 0° C. was added solid KI (7.6 g, 0.36 mole) and solid I$_2$ (6.0 g, 0.030 mole). The reaction mixture was stirred for 2 h, and then poured into H$_2$O. The aqueous mixture was extracted three times with Et$_2$O, and the organic extracts were combined. The ether extracts were dried over Na$_2$SO$_4$, filtered, and concentrated. The crude product was dissolved in MeOH (100 mL), conc. HCl (2 mL) was added, and the mixture was heated at reflux overnight. The reaction was cooled to RT and concentrated. The crude methyl ester was dissolved in EtOAc, and washed two times with H$_2$O (50 mL). The EtOAc layer was dried over Na$_2$SO$_4$, filtered, and concentrated. The crude product was purified by preparative HPLC (TMC CombiPrep PDS, 75×30 mm, 25 mL/min, acetonitrile: H$_2$O, UV detection at 254 nm) to give 2.67 g (29% yield) of title compound as a white solid. MS(ESI) 292.8 (M+).

b) 2-(2-hydroxy-ethyl)-6-benzofuran acetic acid methyl ester

To a stirring solution of (3-hydroxy-4-iodo-phenyl)-acetic acid methyl ester (1.04 g, 0.0035 mole) and 3-butyn-1-ol (0.5 g, 0.007 mole) in a 3:1 solution of toluene/Et$_3$N (25 mL) was added PPh$_3$ (70 mg, 0.26 mmol), CuI (68 mg, 0.35 mmol), and Pd(PPh$_3$)$_2$Cl$_2$ (50 mg, 0.07 mmol). The mixture was heated at 118° C. for 1 h and then cooled to RT. To the reaction mixture was added florisil (2 g) and the mixture was filtered through a fritted funnel. The crude benzofuran was concentrated and subjected to column chromatography over silica gel (silica gel 60, EM Science) using 40% EtOAc: hexane as eluent to afford 0.59 g (71% yield) of the title compound as an oil. MS (ESI) 235.0 (M+H+).

c) 2-{2-[(2,2-diphenylethyl)amino]-ethyl}-6-benzofuran acetic acid methyl ester

To a stirring solution 2-[2-(2-hydroxy-ethyl)-benzofuran] acetic acid methyl ester (0.33 g, 0.0014 mole) in CH$_2$Cl$_2$ (15 mL) at 0° C. was added Et$_3$N (0.21 mL, 0.0015 mole) and methanesulfonyl chloride (0.12 mL, 0.0015 mole). The reaction mixture was stirred for 3 h at 0° C. The mixture was then poured into cold H$_2$O, and extracted two times with CH$_2$Cl$_2$ (30 mL). The CH$_2$Cl$_2$ extracts were washed with saturated aqueous NaCl, dried over Na$_2$SO$_4$, filtered, and concentrated in vacuo. The crude mesylate (prepared above) was dissolved in CH$_3$CN (25 mL), and the following reagents were added to the solution: solid K$_2$CO$_3$ (194 mg, 1.41 mmol) and N-2,2-diphenylethylamine (0.55 g, 0.0014 mole). The reaction mixture was heated overnight at 88° C. The mixture was filtered through a fritted funnel and concentrated. The crude product was purified by preparative HPLC (TMC CombiPrep PDS, 75×30 mm, 25 mL/min, acetonitrile: H$_2$O, UV detection at 254 nm) to give 125 mg (15% yield) of the title compound as a viscous oil. MS(ESI) 400.0 (M+H+).

d) 2-{2-[[2-Chloro-3-(trifluoromethyl)benzyl](2,2-diphenylethyl)amino]-ethyl}-6-benzofuran acetic acid methyl ester To a stirring solution of 2-{2-[(2,2-diphenylethyl)amino]-ethyl}-6-benzofuran acetic acid methyl ester (160 mg, 0.39 mmol) and 2-chloro-3-trifluoromethylbenzaldehyde (81 mg, 0.39 mmol) in CH$_2$Cl$_2$ (4 mL) was added sodium triacetoxyborohydride (91 mg, 0.43 mmol) and two drops of glacial acetic acid. The mixture was stirred for 4 h, and was diluted with EtOAc (10 mL). The mixture was washed with saturated aqueous NH$_4$Cl, saturated aqueous NaHCO$_3$, and saturated aqueous NaCl. The organic layer was dried over Na$_2$SO$_4$, filtered, and concentrated. The crude product was purified by column chromatography over silica (Silica gel 60, EM Science) using 10% EtOAc: Hexane as eluent to afford 0.15 g (64%) of the title compound as an oil. MS(ESI) 606.2 (M+).

e) 2-[2-[[2-Chloro-3-(trifluoromethyl)benzyl](2,2-diphenylethyl)amino]-ethyl}-6-benzofuran acetic acid hydrochloride To a stirring solution of 2-{2-[[2-chloro-3-(trifluoromethyl)benzyl](2,2-diphenylethyl)amino]-ethyl}-6-benzofuran acetic acid methyl ester (150 mg, 0.25 mmol) in a 4:1 H$_2$O/THF (3 mL) solution at 0° C. was added LiOH—H$_2$O (23 mg, 0.55 mmol). The reaction mixture was warmed to RT and stirred overnight. The reaction mixture was concentrated to remove the THF and was diluted with H$_2$O (5 mL). The aqueous solution was acidified with 1 N HCl (10 mL) and extracted three times with EtOAc. The EtOAc extracts were dried over Na$_2$SO$_4$, filtered, and concentrated. The resulting tertiary amine was dissolved in Et$_2$O and acidified with 1 N HCl in Et$_2$O. The solution was stirred for 20 min. and then concentrated to afford 122 mg (78% yield) of the title compound as a white solid. MS(ESI) 592.0.(M+).

EXAMPLE 11

2-[2-{[(2,3-Methylenedioxy)benzyl](2,2-diphenyl-ethyl)amino}ethyl]-6-benzofuran acetic acid hydrochloride

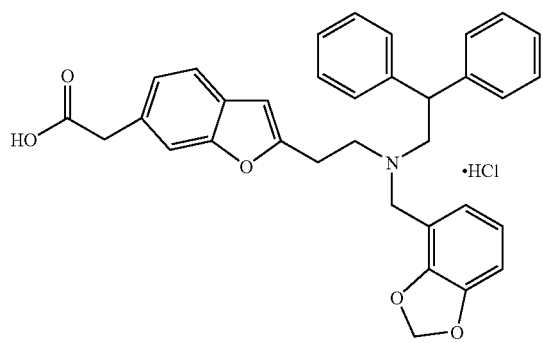

Following the procedure of Example 10(a)-(e) except (2,3-methylenedioxy)benzaldehyde was used in step 10(d) instead of 2-chloro-3-trifluoromethylbenzaldehyde, the title compound was prepared as a white solid (3% overall). MS (ESI) 534.2 (M+H$^+$).

EXAMPLE 12

2-[2-{[(2,4-dimethoxy)benzyl](2,2-diphenylethyl)amino}ethyl]-6-benzofuran acetic acid hydrochloride

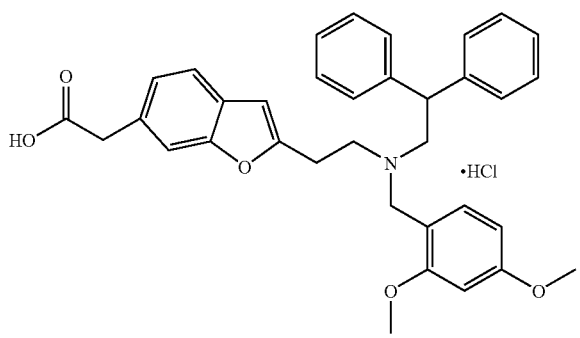

Following the procedure of Example 10(a)-(e) except (2,4-di-methoxy)benzaldehyde was used in step 10(d) instead of 2-chloro-3-trifluoromethylbenzaldehyde, the title compound was prepared as a white solid (4% overall). MS (ESI) 550.2 (M+H$^+$).

EXAMPLE 13

2-{2-[(4-Methoxy-benzyl)(2,2-diphenylethyl)amino]-ethyl}-6-benzofuran acetic acid hydrochloride a) N-(2,2-Diphenylethyl)-N-(4-methoxy-benzyl)amine To a stirring solution of 4-methoxybenzylamine (1.4 g, 0.010 mole) and 2,2-diphenylacetaldehyde (2.0 g, 0.010 mole) in dichloromethane (50 mL) was added sodium triacetoxyborohydride (2.38 g, 0.011 mole) and acetic acid (2.0 mL). The reaction mixture was stirred overnight. The reaction mixture was concentrated and the residue was dissolved in EtOAc. The EtOAc solution was washed with saturated aqueous NaHCO$_3$. The organic extracts were dried over Na$_2$SO$_4$, filtered, and concentrated. The crude mixture was subjected to column chromatography over silica gel (silica gel 60, EM Science) using 30% EtOAc: Hexane as eluent to afford 1.75 g (54% yield) of the title compound as a yellow oil. MS (ESI) 318.0 (M+H$^+$).

b) 2-{2-[(4-Methoxy-benzyl)(2,2-diphenylethyl)amino]-ethyl}-6-benzofuran acetic acid methyl ester Following the procedure of Example 10-step 10(c), except N-(2,2-diphenylethyl)-N-(4-methoxy-benzyl)amine was used instead of N-2,2-diphenylethylamine the title compound was prepared as a white solid (45 mg, 27% overall). MS(ESI) 534.0 (M+H$^+$).

c) 2-{2-[(4-Methoxy-benzyl)(2,2-diphenylethyl)amino]-ethyl}-6-benzofuran acetic acid hydrochloride Following the procedure of Example 10-step 10(e), except 2-{2-[(4-methoxy-benzyl)(2,2-diphenylethyl)amino]-ethyl}-6-benzofuran acetic acid methyl ester was used in step 10(e) instead of 2-{2-[[2-chloro-3-(trifluoromethyl)benzyl](2,2-diphenylethyl)amino]-ethyl}-6-benzofuran acetic acid methyl ester, the title compound was prepared as a white solid (42 mg, 86%). MS (ESI) 520.2 (M+H$^+$).

EXAMPLE 14

2-{2-[(2-Chloro-3-(trifluoromethyl)-benzyl)-(2,2-diphenylethyl-amino]ethyl}-benzofuran-6-yl)-N-furan-2-yl methyl-acetamide hydrochloride

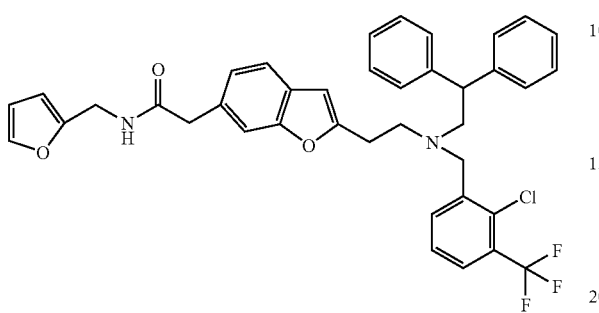

To a stirring mixture of 2-{2-[(2-chloro-3-(trifluoromethyl)-benzyl)-(2,2-diphenylethyl)-amino]-ethyl}-benzofuran-6-yl)- acetic acid (0.19 g, 0.32 mmol), furfurylamine (0.031 g, 0.32 mmol) and acetonitrile (5 mL) was added BOP reagent (0.146 g, 0.33 mmol). After stirring overnight at RT, the reaction mixture was diluted with EtOAc and washed with saturated NaHCO$_3$, water, 0.01 N HCl (aq.) and brine. The organic extract was dried over MgSO$_4$ and filtered. After concentration of the filtrate in vacuo, the crude product was purified by column chromatography over silica gel (silica gel 60, EM Science ) using 30% EtOAc:hexane as eluent to afford 0.166 g (78%) of the title compound as an oil. MS(ESI) 671.2 (M+H$^+$)

EXAMPLE 15

2-{2-[(2,4-Dimethoxy-benzyl)(2,2-diphenylethyl)-amino]ethyl}-benzofuran-6-yl)-N-furan-2-yl methyl-acetamide hydrochloride

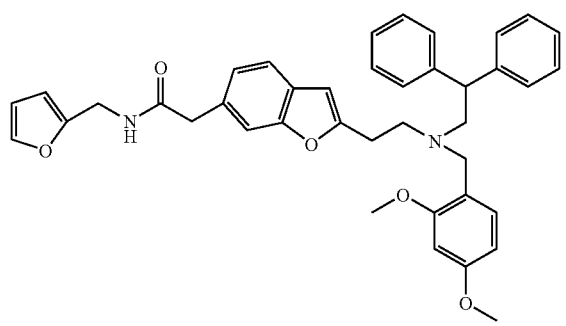

Following the procedure of Example 14 (above) except 2-{2-[(2,4-dimethoxy-benzyl)(2,2-diphenylethyl-amino]ethyl}-benzofuran-6-yl)- acetic acid (Example 12) was used instead of 2-{2-[(2-chloro-3-(trifluoromethyl)-benzyl) (2,2-diphenylethyl-amino]ethyl}-benzofuran-6-yl)-acetic acid the title compound was obtained as a foam (25%). MS(ESI): 629.4 (M+H$^+$).

EXAMPLE 16

2-{2-[(2(Chloro-3-(trifluoromethyl)-benzyl)(2,2-diphenylethyl-amino]ethyl}-benzofuran-6-yl)-acetamide hydrochloride

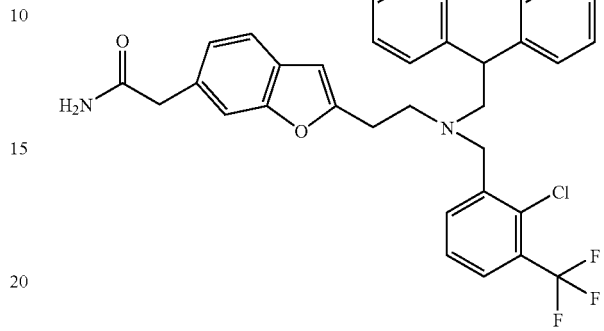

Following the procedure of Example 14 except NH$_3$ in dioxane (0.5 M) was used instead of furfurylamine, the title compound was obtained as a foam (44%). MS(ESI): 591.2 (M+H$^+$)

EXAMPLE 17

(Racemic) 2-{3-[(2-Chloro-3-(trifluoromethyl)-benzyl)-(2-phenyl-propyl)-amino]-propyl}-benzofuran-6-yl)-acetic acid hydrochloride

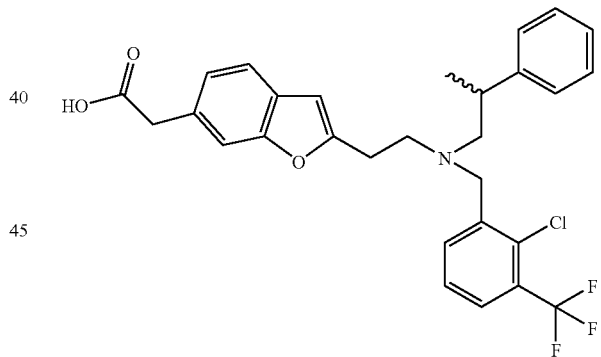

a) [2-(2-azido-ethyl)-benzofuran-6-yl]-acetic acid methyl ester

To a stirring solution 2-[2-(2-hydroxy-ethyl)-benzofuran] acetic acid methyl ester (0.33 g, 0.0014 mol-Example 10 steps (a)-(b)) in CH$_2$Cl$_2$ (15 mL) at 0° C. was added Et$_3$N (0.21 mL, 0.0015 mole) and methanesulfonyl chloride (0.12 mL, 0.0015 mole). The reaction mixture was stirred for 3 h at 0° C. The mixture was then poured into cold H$_2$O, and extracted two times with CH$_2$Cl$_2$ (30 mL). The CH$_2$Cl$_2$ extracts were washed with saturated aqueous NaCl, dried over Na$_2$SO$_4$, filtered, and concentrated in vacuo to afford the corresponding mesylate.

To a stirring solution of the mesylate (0.53 g, 1.71 mmol) in acetonitrile (15 ml) was added sodium azide (0.16 g, 2.56 mmol). The reaction was heated to 85° C. for 1.5 h and then cooled to room temperature. The reaction mixture was poured into H$_2$O (50 ml) and extracted twice with ethyl acetate. The organic extracts were dried over Na$_2$SO$_4$, filtered, and concentrated. The crude product was subjected to column chromatography over silica gel (silica gel 60, EM Science) using 15% EtOAc:hexane as eluent to afford the title compound as a clear oil, 380 mg (85%). MS (ESI) 260.0 (M–H$^+$).

b) 2-{2-[2-Phenyl-propylamino]-ethyl}-6-benzofuran acetic acid methyl ester

To a stirring solution of [2-(2-azido-ethyl)-benzofuran-6-yl]-acetic acid methyl ester (380 mg, 1.45 mmol) in MeOH (7 ml) was added 10% palladium on carbon (30 mg) and the reaction mixture was hydrogenated at atomospheric pressure for 1 h. The mixture was filtered, concentrated, and the crude amine was used in the subsequent step without further purification. MS (ESI) 234.0 (M+H$^+$)

To a stirring solution of the crude amine (above) in CH$_2$Cl$_2$ (10 ml) was added 2-phenyl-propionaldehyde (0.20 ml, 1.52 mmol). To this mixture was added TFA (1 ml) and sodium triacetoxyborohydride (0.4 g, 1.9 mmol) and the reaction mixture was stirred overnight. The reaction mixture was poured into H$_2$O (20 ml) and extracted twice with ethyl acetate. The organic extracts were dried over Na$_2$SO$_4$, filtered, and concentrated. The crude product was subjected to column chromatography over silica gel (silica gel 60, EM Science) using 30% EtOAc:hexane as eluent to afford the title compound as a yellow oil, 0.15 g (30%). MS (ESI) 352.4 (M+H$^+$).

c) 2-{3-[(2-Chloro-3-(trifluoromethyl)-benzyl)-(2-phenyl-propyl)-amino]-propyl}-benzofuran-6-yl)-acetic acid hydrochloride Following the procedure of Example 10(d)-(e) except 2-{2-[2-phenyl-propylamino]-ethyl}-6-benzofuran acetic acid methyl ester was employed in step (d) instead of 2-{2-[(2,2-diphenylethyl)amino]-ethyl}-6-benzofuran acetic acid methyl ester the title compound was prepared as a white solid, 38 mg (51%). MS (ESI) 529.8 (M+H$^+$).

EXAMPLE 18

2-(2-{3-[(2-Chloro-3-(trifluoromethyl)-benzyl-(2,2-diphenylethyl)-amino]-propyl)benzofuran-6-yl)-ethanol hydrochloride

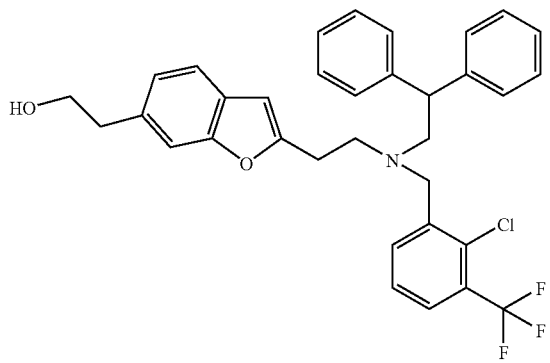

To a stirring mixture of 2-{2-[[2-chloro-3-(trifluoromethyl)benzyl](2,2-diphenylethyl)amino-ethyl}-6-benzofuran acetic acid methyl ester (0.1 g, 0.165 mmol-Example 10(a)-(c)) and ether (15 mL) at −15° C. was added LAH (1 M in THF, 0.5 mL, 0.5 mmol) dropwise. After stirring for 1 h, the reaction mixture was quenched with saturated aqueous NH$_4$Cl and stirred for 15 min. MgSO$_4$ was added and the heterogenous mixture was filtered. The filtrate was concentrated in vacuo and the resulting oil was converted to the HCl salt using 1.0 M HCl/ether to provide the title compound as a white solid, 65 mg (65%) MS (ESI) 578.4 (M+H$^+$).

EXAMPLE 19

2-(2-{3-[(2,4Dimethoxy)-benzyl-(2,2-diphenyl-ethyl)-amino]-propyl}-benzofuran-6-yl)-ethanol hydrochloride

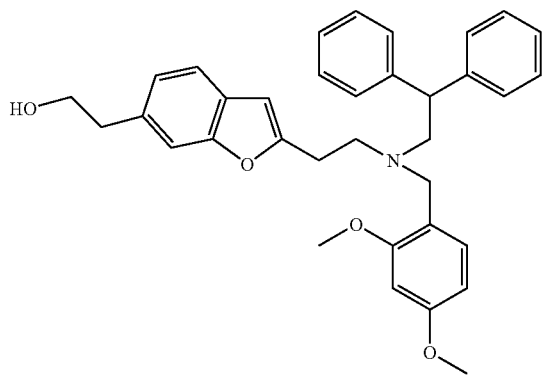

Following the procedure of Example 18 except 2-{2-[[2, 4-dimethoxy)benzyl](2,2-diphenylethyl)amino-ethyl}-6-benzofuran acetic acid methyl ester (Example 12) was used instead of 2-{2-[[2-chloro-3-(trifluoromethyl)benzyl](2,2-diphenylethyl)amino-ethyl}-6-benzofuran acetic acid methyl ester the title compound was prepared as a white solid (66%). MS (ESI) 536.2 (M+H$^+$).

EXAMPLE 20

2-{3-[(2-Chloro-3-(trifluoromethyl)-benzyl)-((R)-2-phenyl-propyl)-amino]-propyl}-benzofuran-6-yl)-acetic acid hydrochloride

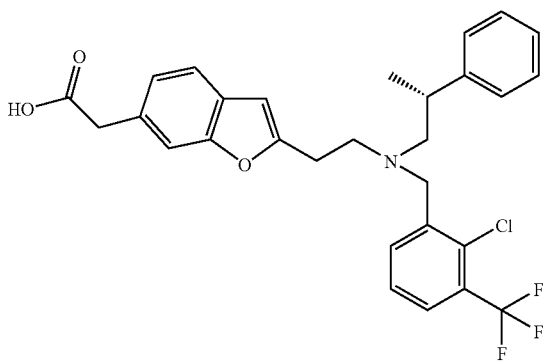

Following the procedure of Example 10(a-e) except (R)-(+)-β-methylphenylethylamine was used instead of N-2,2-diphenylethylamine in step 10(c) the title compound was prepared as a white solid (2% overall). MS (ESI) 530.2 (M+H⁺).

EXAMPLE 21

2-{3-[(2-Chloro-3-(trifluoromethyl)-benzyl)-((S)-2-phenyl-propyl)-amino]-propyl)benzofuran-6-yl)-acetic acid hydrochloride

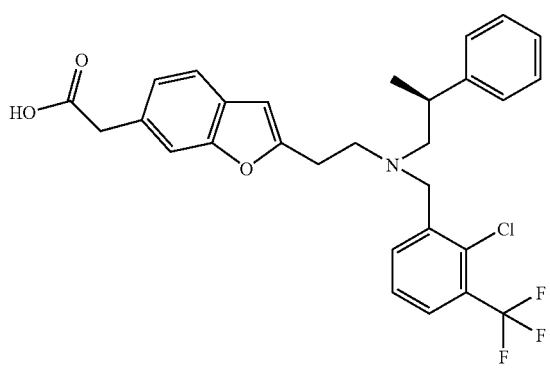

Following the procedure of Example 10(a-e) except (S)-(−)-β-methylphenylethylamine was used instead of N-2,2-diphenylethylamine in step 10(c) the title compound was prepared as a white solid (1.5% overall). MS (ESI) 530.2 (M+H⁺).

EXAMPLE 22

(2-Chloro-3-trifluoromethyl-benzyl)-(2,2-diphenyl-ethyl)-[3-(6-{2-[(furan-2-ylmethyl)-amino]-ethyl-benzofuran-2-yl)-propyl]-amine dihydrochloride

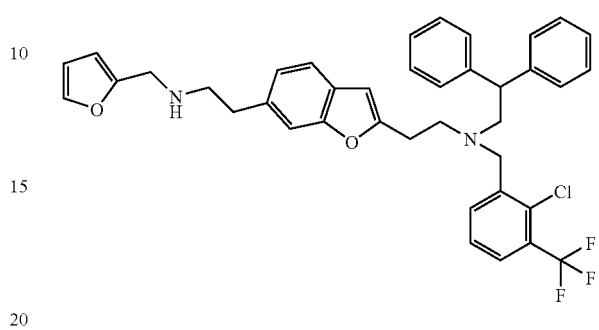

To a stirring solution of 2-{2-[(2-chloro-3-(trifluoromethyl)-benzyl)-(2,2-diphenylethyl-amino]ethyl}-benzofuran-6-yl)-N-furan-2-yl methyl-acetamide (0.16 g, 0.24 mmol-Example 14) in THF (1.5 mL) was added DIBAL-H (1.5 M in toluene, 0.32 mL, 0.48 mmol). After stirring under argon overnight, the reaction mixture was quenched with saturated NH₄Cl and extracted with EtOAc. The organic layer was washed with water, brine and dried over MgSO₄. The organic extracts were filtered and then concentrated in vacuo. The crude product was purified by column chromatography over silica gel (silica gel 60, EM Science) using 0.5% MeOH: 0.1% conc. NH₄OH: dichloromethane to afford the title compound as an oil. The free base was converted to the HCl salt using 0.1 M HCl/ether to provide the title compound as a white solid, 31%. MS (ESI) 657.2 (M+H⁺).

The above description fully discloses how to make and use the present invention. However, this invention is not limited to the particular embodiments described hereinabove, but includes all modification thereof within the scope of the appended claims and their equivalents. Those skilled in the art will recognize through routine experimentation that various changes and modifications can be made without departing from the scope of this invention. The various references to journals, patents and other patent applications that are cited herein are incorporated by reference herein as though fully set forth.

---

What is claimed is:

1. A compound of Formula I:

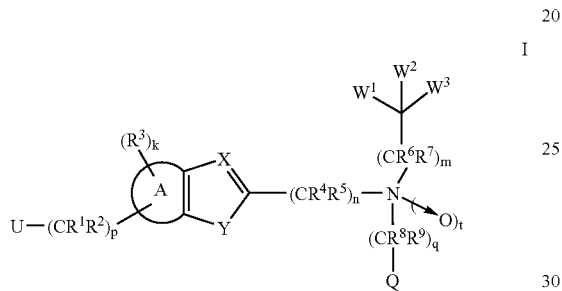

I wherein:

X is CH or N;

Y is $N(R^{10})$, O, or S, wherein t is 0 or 1 when Y is $N(R^{10})$ or O, and t is 0 when Y is S;

U is selected from halo, $-OR^{10}$, $-NR^{14}R^{15}$, nitro, cyano, $-COOR^{10}$, $-COR^{13}$, $-OCOR^{13}$, $-CONR^{14}R^{15}$, $-N(R^{14})COR^{13}$, $-SO_3H$, $-SO_2NR^{14}R^{15}$, $-C(=NR^{17})NR^{14}R^{15}$, $-N(R^{14})SO_2R^{16}$, and a 5 or 6-membered heterocyclic group;

A is a phenyl fused ring moiety or a pyridyl fused ring moiety, wherein when A is a phenyl ring moiety, k is 0-3 and t is 0 or 1 and when A is a pyridyl ring moiety, k is 0-2 and t is 0;

$W^1$ is selected from $C_3-C_8$ cycloalkyl, aryl and Het, wherein said $C_3-C_8$ cycloalkyl, Ar and Het are optionally unsubstituted or substituted with one or more groups independently selected from halo, cyano, nitro, $C_1-C_6$ alkyl, $C_3-C_6$ alkenyl, $C_3-C_6$ alkynyl, $-C_0-C_6$ alkyl-$CO_2R^{10}$, $-C_0-C_6$ alkyl-$C(O)SR^{10}$, $-C_0-C_6$ alkyl-$CONR^{11}R^{12}$, $-C_0-C_6$ alkyl-$COR^{13}$, $-C_0-C_6$ alkyl-$NR^{11}R^{12}$, $-C_0-C_6$ alkyl-$SR^{10}$, $-C_0-C_6$ alkyl-$OR^{10}$, $-C_0-C_6$ alkyl-$SO_3H$, $-C_0-C_6$ alkyl-$SO_2NR^{11}R^{12}$, $-C_0-C_6$ alkyl-$SO_2R^{10}$, $-C_0-C_6$ alkyl-$SOR^{13}$, $-C_0-C_6$ alkyl-$OCOR^{13}$, $-C_0-C_6$ alkyl-$OC(O)NR^{11}R^{12}$, $-C_0-C_6$ alkyl-$OC(O)OR^{13}$, $-C_0-C_6$ alkyl-$NR^{11}C(O)OR^{13}$, $-C_0-C_6$ alkyl-$NR^{11}C(O)NR^{11}R^{12}$, and $-C_0-C_6$ alkyl-$NR^{11}COR^{13}$, where said $C_1-C_6$ alkyl, is optionally unsubstituted or substituted by one or more halo substituents;

$W^2$ is selected from H, halo, $C_1-C_6$ alkyl, $C_2-C_6$ alkenyl, $C_2-C_6$ alkynyl, $-C_0-C_6$ alkyl-$NR^{11}R^{12}$, $-C_0-C_6$ alkyl-$SR^{10}$, $-C_0-C_6$ alkyl-$OR^{10}$, $-C_0-C_6$ alkyl-$CO_2R^{10}$, $-C_0-C_6$ alkyl-$C(O)SR^{10}$, $-C_0-C_6$ alkyl-$CONR^{11}R^{12}$, $-C_0-C_6$ alkyl-$COR^{13}$, $-C_0-C_6$ alkyl-$OCOR^{13}$, $-C_0-C_6$ alkyl-$OCONR^{11}R^{12}$, $-C_0-C_6$ alkyl-$NR^{11}CONR^{11}R^{12}$, $-C_0-C_6$ alkyl-$NR^{11}COR^{13}$, $-C_0-C_6$ alkyl-Het, $-C_0-C_6$ alkyl-Ar and $-C_0-C_6$ alkyl-$C_3-C_7$ cycloalkyl, wherein said $C_1-C_6$ alkyl is optionally unsubstituted or substituted by one or more halo substituents, and wherein the $C_3-C_7$ cycloalkyl, Ar and Het moieties of said $-C_0-C_6$ alkyl-Het, $-C_0-C_6$ alkyl-Ar and $-C_0-C_6$ alkyl-$C_3-C_7$ cycloalkyl are optionally unsubstituted or substituted with one or more groups independently selected from halo, cyano, nitro, $C_1-C_6$ alkyl, $C_3-C_6$ alkenyl, $C_3-C_6$ alkynyl, $-C_0-C_6$ alkyl-$CO_2R^{10}$, $-C_0-C_6$ alkyl-$C(O)SR^{10}$, $-C_0-C_6$ alkyl-$CONR^{11}R^{12}$, $-C_0-C_6$ alkyl-$COR^{13}$, $-C_0-C_6$ alkyl-$NR^{11}R^{12}$, $-C_0-C_6$ alkyl-$SR^{10}$, $-C_0-C_6$ alkyl-$OR^{10}$, $-C_0-C_6$ alkyl-$SO_3H$, $-C_0-C_6$ alkyl-$SO_2NR^{11}R^{12}$, $-C_0-C_6$ alkyl-$SO_2R^{10}$, $-C_0-C_6$ alkyl-$SOR^{13}$, $-C_0-C_6$ alkyl-$OCOR^{13}$, $-C_0-C_6$ alkyl-$OC(O)NR^{11}R^{12}$, $-C_0-C_6$ alkyl-$OC(O)OR^{13}$, $-C_0-C_6$ alkyl-$NR^{11}C(O)OR^{13}$, $-C_0-C_6$ alkyl-$NR^{11}C(O)NR^{11}R^{12}$, and $-C_0-C_6$ alkyl-$NR^{11}COR^{13}$, where said $C_1-C_6$ alkyl, is optionally unsubstituted or substituted by one or more halo substituents;

$W^3$ is selected from the group consisting of: H, halo, $C_1-C_6$ alkyl, $-C_0-C_6$ alkyl-$NR^{11}R^{12}$, $-C_0-C_6$ alkyl-$SR^{10}$, $-C_0-C_6$ alkyl-$OR^{10}$, $-C_0-C_6$ alkyl-$CO_2R^{10}$, $-C_0-C_6$ alkyl-$C(O)SR^{10}$, $-C_0-C_6$ alkyl-$CONR^{11}R^{12}$, $-C_0-C_6$ alkyl-$COR^{13}$, $-C_0-C_6$ alkyl-$OCOR^{13}$, $-C_0-C_6$ alkyl-$OCONR^{11}R^{12}$, $-C_0-C_6$ alkyl-$NR^{11}CONR^{11}R^{12}$, $-C_0-C_6$ alkyl-$NR^{11}COR^{13}$, $-C_0-C_6$ alkyl-Het, $-C_1-C_6$ alkyl-Ar and $-C_1-C_6$ alkyl-$C_3-C_7$ cycloalkyl, wherein said $C_1-C_6$ alkyl is optionally unsubstituted or substituted by one or more halo substituents;

Q is selected from $C_3-C_8$ cycloalkyl, Ar and Het; wherein said $C_3-C_8$ cycloalkyl, Ar and Het are optionally unsubstituted or substituted with one or more groups independently selected from halo, cyano, nitro, $C_1-C_6$ alkyl, $C_3-C_6$ alkenyl, $C_3-C_6$ alkynyl, $-C_0-C_6$ alkyl-$CO_2R^{10}$, $-C_0-C_6$ alkyl-$C(O)SR^{10}$, $-C_0-C_6$ alkyl-$CONR^{11}R^{12}$, $-C_0-C_6$ alkyl-$COR^{13}$, $-C_0-C_6$ alkyl-$NR^{11}R^{12}$, $-C_0-C_6$ alkyl-$SR^{10}$, $-C_0-C_6$ alkyl-$OR^{10}$, $-C_0-C_6$ alkyl-$SO_3H$, $-C_0-C_6$ alkyl-$SO_2NR^{11}R^{12}$, $-C_0-C_6$ alkyl-$SO_2R^{10}$, $-C_0-C_6$ alkyl-$SOR^{13}$, $-C_0-C_6$ alkyl-$OCOR^{13}$, $-C_0-C_6$ alkyl-$OC(O)NR^{11}R^{12}$, $-C_0-C_6$ alkyl-$OC(O)OR^{13}$, $-C_0-C_6$ alkyl-$NR^{11}C(O)OR^{13}$, $-C_0-C_6$ alkyl-$NR^{11}C(O)NR^{11}R^{12}$, and $-C_0-C_6$ alkyl-$NR^{11}COR^{13}$, where said $C_1-C_6$ alkyl is optionally unsubstituted or substituted by one or more halo substituents;

p is 0-8;

n is 2;

m is 0 or 1;

q is 0 or 1;

t is 0 or 1;

each $R^1$ and $R^2$ are independently selected from H, halo, $C_1$-$C_6$ alkyl, $C_3$-$C_6$ alkenyl, $C_3$-$C_6$ alkynyl, —$C_0$-$C_6$ alkyl-$NR^{11}R^{12}$, —$C_0$-$C_6$ alkyl-$OR^{10}$, —$C_0$-$C_6$ alkyl-$SR^{10}$, —$C_1$-$C_6$ alkyl-Het, —$C_1$-$C_6$ alkyl-Ar and —$C_1$-$C_6$ alkyl-$C_3$-$C_7$ cycloalkyl, or $R^1$ and $R^2$ together with the carbon to which they are attached form a 3-5 membered carbocyclic or heterocyclic ring, wherein said heterocyclic ring contains one, or more heteroatoms selected from N, O, and S, where said $C_1$-$C_6$ alkyl is optionally unsubstituted or substituted by one or more halo substituents;

each $R^3$ is the same or different and is independently selected from halo, cyano, nitro, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-$CO_2R^{10}$, —$C_0$-$C_6$ alkyl-C(O)$SR^{10}$, —$C_0$-$C_6$ alkyl-$CONR^{11}R^{12}$, —$C_0$-$C_6$ alkyl-$COR^{13}$, —$C_0$-$C_6$ alkyl-$NR^{11}R^{12}$, —$C_0$-$C_6$ alkyl-$SR^{10}$, —$C_0$-$C_6$ alkyl-$OR^{10}$, —$C_0$-$C_6$ alkyl-$SO_3H$, —$C_0$-$C_6$ alkyl-$SO_2NR^{11}R^{12}$, —$C_0$-$C_6$ alkyl-$SO_2R^{10}$, —$C_0$-$C_6$ alkyl-$SOR^{13}$, —$C_0$-$C_6$ alkyl-$OCOR^{13}$, —$C_0$-$C_6$ alkyl-OC(O)$NR^{11}R^{12}$, —$C_0$-$C_6$ alkyl-OC(O)$OR^{13}$, —$C_0$-$C_6$ alkyl-$NR^{11}C(O)OR^{13}$, —$C_0$-$C_6$ alkyl-$NR^{11}C(O)NR^{11}R^{12}$, and —$C_0$-$C_6$ alkyl-$NR^{11}COR^{13}$, wherein said $C_1$-$C_6$ alkyl is optionally unsubstituted or substituted by one or more halo substituents;

each $R^4$ and $R^5$ is independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^6$ and $R^7$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^8$ and $R^9$ are each independently selected from H, halo, $C_1$-$C_6$ alkyl, —$C_0$-$C_6$ alkyl-Het, —$C_0$-$C_6$ alkyl-Ar and —$C_0$-$C_6$ alkyl-$C_3$-$C_7$ cycloalkyl;

$R^{10}$ is selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_q$-$C_6$ alkyl-$C_3$-$C_7$ cycloalkyl;

each $R^{11}$ and each $R^{12}$ are independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl, or $R^{11}$ and $R^{12}$ together with the nitrogen to which they are attached form a 4-7 membered heterocyclic ring which optionally contains one or more additional heteroatoms selected from N, O, and S;

$R^{13}$ is selected from $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het and —$C_0$-$C_6$ alkyl-$C_3$-$C_7$ cycloalkyl;

$R^{14}$ and $R^{15}$ are each independently selected from H, $C_1$-$C_6$ alkyl, $C_3$-$C_6$ alkenyl, $C_3$-$C_6$ alkynyl, —$C_0$-$C_6$ alkyl-Ar, —$C_0$-$C_6$ alkyl-Het, —$C_0$-$C_6$ alkyl-$C_3$-$C_7$ cycloalkyl, —$C_0$-$C_6$ alkyl-O—Ar, —$C_0$-$C_6$ alkyl-O-Het, —$C_0$-$C_6$ alkyl-O—$C_3$-$C_7$ cycloalkyl, —$C_0$-$C_6$ alkyl-S(O)$_x$-$C_1$-$C_6$ alkyl, —$C_0$-$C_6$ alkyl-S(O)$_x$—Ar, —$C_0$-$C_6$ alkyl-S(O)$_x$-Het, —$C_0$-$C_6$ alkyl-S(O)$_x$-$C_3$-$C_7$ cycloalkyl, —$C_0$-$C_6$ alkyl-NH—Ar, —$C_0$-$C_6$ alkyl-NH-Het, —$C_0$-$C_6$ alkyl-NH-$C_3$-$C_7$ cycloalkyl, —$C_0$-$C_6$ alkyl-N($C_1$-$C_4$ alkyl)-Ar, —$C_0$-$C_6$ alkyl-N($C_1$-$C_4$ alkyl)-Het, —$C_0$-$C_6$ alkyl-N($C_1$-$C_4$ alkyl)-$C_3$-$C_7$ cycloalkyl, —$C_0$-$C_6$ alkyl-Ar, —$C_0$-$C_6$ alkyl-Het and —$C_0$-$C_6$ alkyl-$C_3$-$C_7$ cycloalkyl, where x is 0, 1 or 2, or $R^{14}$ and $R^{15}$, together with the nitrogen to which they are attached, form a 4-7 membered heterocyclic ring which optionally contains one or more additional heteroatoms selected from N, O, and S, wherein said $C_1$-$C_6$ alkyl is optionally substituted by one or more of the substituents independently selected from the group halo, —OH, —SH, —$NH_2$, —NH(unsubstituted $C_1$-$C_6$ alkyl), —N(unsubstituted $C_1$-$C_6$ alkyl)(unsubstituted $C_1$-$C_6$ alkyl), unsubstituted —O$C_1$-$C_6$ alkyl, —$CO_2H$, —$CO_2$(unsubstituted $C_1$-$C_6$ alkyl), —$CONH_2$, —CONH(unsubstituted $C_1$-$C_6$ alkyl), —CON(unsubstituted $C_1$-$C_6$ alkyl)(unsubstituted $C_1$-$C_6$ alkyl), —$SO_3H$, —$SO_2NH_2$, —$SO_2NH$(unsubstituted $C_1$-$C_6$ alkyl) and —$SO_2N$(unsubstituted $C_1$-$C_6$ alkyl)(unsubstituted $C_1$-$C_6$ alkyl);

$R^{16}$ is $C_1$-$C_6$ alkyl, —$C_0$-$C_6$ alkyl-Ar or —$C_0$-$C_6$ alkyl-Het; and $R^{17}$ is H, $C_1$-$C_6$ alkyl, —$C_0$-$C_6$ alkyl-Ar or —$C_0$-$C_6$ alkyl-Het;

or a pharmaceutically acceptable salt or solvate thereof.

2. The compound according to claim 1, wherein p is 0, 1 or 2.

3. The compound according to claim 1, wherein t is 0.

4. The compound according to claim 1, wherein $R^1$ and $R^2$ are each H.

5. The compound according to claim 1, wherein A is a phenyl fused ring.

6. The compound according to claim 1, wherein k is 0.

7. The compound according to claim 1, wherein U is —$OR^{10}$, —$COOR^{10}$, —$CONR^{11}R^{12}$ or —$NR^{11}R^{12}$.

8. The compound according to claim 1, wherein U is —OH, —COOH, —$CONH_2$, —CON(H)$CH_2$-furan-2-yl, or —N(H)$CH_2$-furan-2-yl.

9. The compound according to claim 1, wherein q is 1.

10. The compound according to claim 1, wherein $R^8$ and $R^9$ are each H.

11. The compound according to claim 1, wherein Q is a substituted phenyl group, containing one or two substituents selected from halo, $C_1$-$C_4$ alkoxy; and $C_1$-$C_4$ alkyl or Q is a 1,3-benzodioxolyl or dihydrobenzofuranyl group.

12. The compound according to claim 1, wherein Q is a phenyl group substituted by one or two substituents selected from chloro, trifluoromethyl and methoxy or is a 1,3-benzodioxolyl or a dihydrobenzofuranyl group.

13. The compound according to claim 1, wherein m is 1 and $R^6$ and $R^7$ are both H.

14. The compound according to claim 1, wherein $W^3$ is H.

15. The compound according to claim 1 wherein $W^1$ and $W^2$ are each unsubstituted phenyl or $W^1$ is unsubstituted phenyl and $W^2$ is methyl.

16. A compound of Formula II:

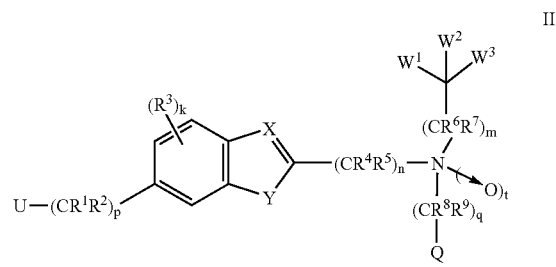

wherein:

X is CH or N;

Y is O, or S;

U is selected from halo, —$OR^{10}$, —$NR^{14}R^{15}$, cyano, —$COOR^{10}$, —$OCOR^{13}$, —$CONR^{14}R^{15}$, —N($R^{14}$)

COR$^{13}$, —SO$_2$NR$^{14}$R$^{15}$, —C(=NH)NR$^{14}$R$^{15}$, and a 5 or 6-membered heterocyclic group;

W$^1$ is selected from C$_3$-C$_8$ cycloalkyl, aryl and Het, wherein said C$_3$-C$_8$ cycloalkyl, Ar and Het are optionally unsubstituted or substituted with one or more groups independently selected from halo, cyano, nitro, C$_1$-C$_6$ alkyl, C$_3$-C$_6$ alkenyl, C$_3$-C$_6$ alkynyl, —C$_0$-C$_4$ alkyl-CO$_2$R$^{10}$, —C$_0$-C$_4$ alkyl-C(O)SR$^{10}$, —C$_0$-C$_4$ alkyl-CONR$^{11}$R$^{12}$, —C$_0$-C$_4$ alkyl-COR$^{13}$, —C$_0$-C$_4$ alkyl-NR$^{11}$R$^{12}$ —C$_0$-C$_4$ alkyl-SR$^{10}$, —C$_0$-C$_4$ alkyl-OR$^{10}$, —C$_0$-C$_4$ alkyl-SO$_3$H, —C$_0$-C$_4$alkyl-SO$_2$NR$^{11}$R$^{12}$, —C$_0$-C$_4$ alkyl-SO$_2$R$^{10}$, —C$_0$-C$_4$ alkyl-SOR$^{13}$, —C$_0$-C$_4$ alkyl-OCOR$^{13}$, —C$_0$-C$_4$ alkyl-OC(O)NR$^{11}$R$^{12}$, —C$_0$-C$_4$ alkyl-OC(O)OR$^{13}$, —C$_0$-C$_4$ alkyl-NR$^{11}$C(O)OR$^{13}$, —C$_0$-C$_4$ alkyl-NR$^{11}$ C(O)NR$^{11}$R$^{12}$, and —C$_0$-C$_4$ alkyl-NR$^{11}$COR$^{13}$, where said C$_1$-C$_6$ alkyl is optionally unsubstituted or substituted by one or more halo substituents;

W$^2$ is selected from H, halo, C$_1$-C$_6$ alkyl, C$_2$-C$_6$ alkenyl, C$_2$-C$_6$ alkynyl, —C$_0$-C$_4$ alkyl-NR$^{11}$R$^{12}$, —C$_0$-C$_4$ alkyl-SR$^{10}$, —C$_0$-C$_4$ alkyl-OR$^{10}$, —C$_0$-C$_4$ alkyl-CO$_2$R$^{10}$, —C$_0$-C$_4$ alkyl-C(O)SR$^{10}$, —C$_0$-C$_4$ alkyl-CONR$^{11}$R$^{12}$, —C$_0$-C$_4$ alkyl-COR$^{13}$, —C$_0$-C$_4$ alkyl-OCOR$^{13}$, —C$_0$-C$_4$ alkyl-OCONR$^{11}$R$^{12}$, —C$_0$-C$_4$ alkyl-NR$^{11}$CONR$^{11}$R$^{12}$, —C$_0$-C$_4$ alkyl-NR$^{11}$COR$^{13}$, —C$_0$-C$_4$ alkyl-Het, —C$_0$-C$_4$ alkyl-Ar and —C$_0$-C$_4$ alkyl-C$_3$-C$_7$ cycloalkyl, wherein said C$_1$-C$_6$ alkyl is optionally unsubstituted or substituted by one or more halo substituents, and wherein the C$_3$-C$_7$ cycloalkyl, Ar and Het moieties of said —C$_0$-C$_4$ alkyl-Het, —C$_0$-C$_4$ alkyl-Ar and —C$_0$-C$_4$ alkyl-C$_3$-C$_7$ cycloalkyl are optionally unsubstituted or substituted with one or more groups independently selected from halo, cyano, nitro, C$_1$-C$_6$ alkyl, C$_3$-C$_6$ alkenyl, C$_3$-C$_6$ alkynyl, —C$_0$-C$_4$ alkyl-CO$_2$R$^{10}$, —C$_0$-C$_4$ alkyl-C(O)SR$^{10}$, —C$_0$-C$_4$ alkyl-CONR$^{11}$R$^{12}$, —C$_0$-C$_4$ alkyl-COR$^{13}$, —C$_0$-C$_4$ alkyl-NR$^{11}$R$^{12}$, —C$_0$-C$_4$ alkyl-SR$^{10}$, —C$_0$-C$_4$ alkyl-OR$^{10}$, —C$_0$-C$_4$ alkyl-SO$_3$H, —C$_0$-C$_4$ alkyl-SO$_2$N$^{11}$R$^{12}$, —C$_0$-C$_4$ alkyl-SO$_2$R$^{10}$, —C$_0$-C$_4$ alkyl-SOR$^{13}$, —C$_0$-C$_4$ alkyl-OCOR$^{13}$, —C$_0$-C$_4$ alkyl-OC(O)NR$^{11}$R$^{12}$, —C$_0$-C$_4$ alkyl-OC(O)OR$^{13}$, —C$_0$-C$_4$ alkyl-NR$^{11}$C(O)OR$^{13}$, —C$_0$-C$_4$ alkyl-NR$^{11}$C(O)NR$^{11}$R$^{12}$, and —C$_0$-C$_4$ alkyl-NR$^{11}$COR$^{13}$, where said C$_1$-C$_6$ alkyl is optionally unsubstituted or substituted by one or more halo substituents;

W$^3$ is selected from the group consisting of: H, halo, C$_1$-C$_6$ alkyl, —C$_0$-C$_4$ alkyl-NR$^{11}$R$^{12}$, —C$_0$-C$_4$ alkyl-SR$^{10}$, —C$_0$-C$_4$ alkyl-OR$^{10}$, —C$_0$-C$_4$ alkyl-CO$_2$R$^{10}$, —C$_0$-C$_4$ alkyl-C(O)SR$^{10}$, —C$_0$-C$_4$ alkyl-CONR$^{11}$R$^{12}$, —C$_0$-C$_4$ alkyl-COR$^{13}$, —C$_0$-C$_4$ alkyl-OCOR$^{13}$, —C$_0$-C$_4$ alkyl-OCONR$^{11}$R$^{12}$, —C$_0$-C$_4$ alkyl-NR$^{11}$CONR$^{11}$R$^{12}$, —C$_0$-C$_4$ alkyl-NR$^{11}$COR$^{13}$, —C$_0$-C$_4$ alkyl-Het, —C$_1$-C$_4$ alkyl-Ar and —C$_1$-C$_4$ alkyl-C$_3$-C$_7$ cycloalkyl, wherein said C$_1$-C$_6$ alkyl is optionally unsubstituted or substituted by one or more halo substituents;

Q is Ar or Het; wherein said Ar and Het are optionally unsubstituted or substituted with one or more groups independently selected from halo, cyano, nitro, C$_1$-C$_6$ alkyl, C$_3$-C$_6$ alkenyl, C$_3$-C$_6$ alkynyl, —C$_0$-C$_4$ alkyl-CO$_2$R$^{10}$, —C$_0$-C$_4$ alkyl-C(O)SR$^{10}$, —C$_0$-C$_4$ alkyl-CONR$^{11}$R$^{12}$, —C$_0$-C$_4$ alkyl-COR$^{13}$, —C$_0$-C$_4$ alkyl-NR$^{11}$R$^{12}$, —C$_0$-C$_4$ alkyl-SR$^{10}$, —C$_0$-C$_4$ alkyl-OR$^{10}$, —C$_0$-C$_4$ alkyl-SO$_3$H, —C$_0$-C$_4$ alkyl-SO$_2$NR$^{11}$R$^{12}$, —C$_0$-C$_4$ alkyl-SO$_2$R$^{10}$, —C$_0$-C$_4$ alkyl-SOR$^{13}$, —C$_0$-C$_4$ alkyl-OCOR$^{13}$, —C$_0$-C$_4$ alkyl-OC(O)NR$^{11}$R$^{12}$, —C$_0$-C$_4$ alkyl-OC(O)OR$^{13}$, —C$_0$-C$_4$ alkyl-NR$^{11}$C(O)OR$^{13}$, —C$_0$-C$_4$ alkyl-NR$^{11}$C(O)NR$^{11}$R$^{12}$, and —C$_0$-C$_4$ alkyl-NR$^{11}$COR$^{13}$, where said C$_1$-C$_6$ alkyl is optionally unsubstituted or substituted by one or more halo substituents, p is 0-4;

n is 2;

m is 0 or 1;

q is 0 or 1;

t is 0;

each R$^1$ and R$^2$ are independently selected from H, fluoro, C$_1$-C$_6$ alkyl, —C$_0$-C$_4$ alkyl-OR$^{10}$, —C$_0$-C$_4$ alkyl-SR$^{10}$, —C$_1$-C$_4$ alkyl-Het, —C$_1$-C$_4$ alkyl-Ar and —C$_1$-C$_4$ alkyl-C$_3$-C$_7$ cycloalkyl, where said C$_1$-C$_6$ alkyl is optionally unsubstituted or substituted by one or more halo substituents;

each R$^3$ is the same or different and is independently selected from halo, cyano, C$_1$-C$_6$ alkyl, —C$_0$-C$_4$ alkyl-NR$^{11}$R$^{12}$, —C$_0$-C$_4$ alkyl-OR$^{10}$, —C$_0$-C$_4$ alkyl-SO$_2$NR$^{11}$R$^{12}$, and —C$_0$-C$_4$ alkyl-CO$_2$H, wherein said C$_1$-C$_6$ alkyl is optionally unsubstituted or substituted by one or more halo substituents;

each R$^4$ and R$^5$ is independently selected from H, fluoro and C$_1$-C$_6$ alkyl;

R$^6$ and R$^7$ are each independently selected from H, fluoro and C$_1$-C$_6$ alkyl;

R$^8$ and R$^9$ are each independently selected from H, fluoro and C$_1$-C$_6$ alkyl;

R$^{10}$ is selected from H, C$_1$-C$_6$ alkyl, —C$_0$-C$_4$ alkyl-Ar, —C$_0$-C$_4$ alkyl-Het and —C$_0$-C$_4$ alkyl-C$_3$-C$_7$ cycloalkyl;

each R$^{11}$ and each R$^{12}$ are independently selected from H, C$_1$-C$_6$ alkyl, —C$_0$-C$_4$ alkyl-Ar, —C$_0$-C$_4$ alkyl-Het and —C$_0$-C$_4$ alkyl-C$_3$-C$_7$ cycloalkyl, or R$^{11}$ and R$^{12}$ together with the nitrogen to which they are attached form a 4-7 membered heterocyclic ring which optionally contains one or more additional heteroatoms selected from N, O, and S;

R$^{13}$ is selected from C$_1$-C$_6$ alkyl, —C$_0$-C$_4$ alkyl-Ar, —C$_0$-C$_4$ alkyl-Het and —C$_0$-C$_4$ alkyl-C$_3$-C$_7$ cycloalkyl;

R$^{14}$ and R$^{15}$ are each independently selected from H, C$_1$-C$_6$ alkyl, C$_3$-C$_6$ alkenyl, C$_3$-C$_6$ alkynyl, —C$_0$-C$_4$ alkyl-Ar, —CO-C$_4$ alkyl-Het, —C$_0$-C$_4$ alkyl-C$_3$-C$_7$ cycloalkyl, —C$_0$-C$_4$ alkyl-O—Ar, —C$_0$-C$_4$ alkyl-O-Het, —C$_0$-C$_4$ alkyl-O—C$_3$-C$_7$ cycloalkyl, —C$_0$-C$_4$ alkyl-S(O)$_x$-C$_1$-C$_6$ alkyl, —C$_0$-C$_4$ alkyl-S(O)$_x$—Ar, —C$_0$-C$_4$ alkyl-S(O)$_x$-Het, —C$_0$-C$_4$ alkyl-S(O)$_x$-C$_3$-C$_7$ cycloalkyl, —C$_0$-C$_4$ alkyl-NH—Ar, —C$_0$-C$_4$ alkyl-NH-Het, —C$_0$-C$_4$ alkyl-NH—C$_3$-C$_7$ cycloalkyl, —C$_0$-C$_4$ alkyl-N(C$_1$-C$_4$ alkyl)-Ar, —C$_0$-C$_4$ alkyl-N(C$_1$-C$_4$ alkyl)-Het, —C$_0$-C$_4$ alkyl-N(C$_1$-C$_4$ alkyl)-C$_3$-C$_7$ cycloalkyl, —C$_0$-C$_4$ alkyl-Ar, —C$_0$-C$_4$ alkyl-Het and —C$_0$-C$_4$ alkyl-C$_3$-C$_7$ cycloalkyl, where x is 0, 1 or 2, or R$^{14}$ and R$^{15}$, together with the nitrogen to which they are attached, form a 4-7 membered heterocyclic ring which optionally contains one or more additional heteroatoms selected from N, O, and S, wherein said C$_1$-C$_6$ alkyl, C$_3$-C$_6$ alkenyl, C$_3$-C$_6$ alkynyl are optionally substituted by one or more of the substituents independently selected from the group halo, —OH, —SH, —NH$_2$, —NH(unsubstituted C$_1$-C$_4$ alkyl), —N(unsubstituted C$_1$-C$_4$ alkyl)(unsubstituted C$_1$-C$_4$ alkyl), unsubstituted —OC$_1$-C$_4$ alkyl, —CO$_2$H, —CO$_2$(unsubstituted C$_1$-C$_4$ alkyl), —CONH$_2$, —CONH(unsubstituted C$_1$-C$_4$ alkyl), —CON(unsubstituted C$_1$-C$_4$ alkyl)(unsubstituted C$_1$-C$_4$ alkyl), —SO$_3$H, —SO$_2$NH$_2$, —SO$_2$NH(unsubstituted C$_1$-C$_4$ alkyl) and —SO$_2$N(unsubstituted C$_1$-C$_4$ alkyl)(unsubstituted C$_1$-C$_4$ alkyl);

or a pharmaceutically acceptable salt or solvate thereof.

17. The compound according to claim 1, wherein: R$^1$, R$^2$, R$^3$, R$^4$, R$^5$, R$^6$, R$^7$, R$^8$ and R$^9$ are each H; U is —OR$^{10}$, —COOR$^{10}$, —CONR$^{11}$R$^{12}$ or —NR$^{11}$R$^{12}$; A is a phenyl fused ring; Q is a substituted phenyl group containing one or two substituents selected from halo, C$_1$-C$_4$ alkoxy and C$_1$-C$_4$ alkyl or Q is a 1,3-benzodioxolyl or a dihydrobenzofuranyl group; p is 1 or 2; n is 2; m is 1; q is 1; k is 0; t is 0; W$^1$ is aryl; W$^2$ is aryl or C$_1$-C$_4$ alkyl; and W$^3$ is H; or a pharmaceutically acceptable salt or solvate thereof.

18. The compound according to claim 1, wherein R$^1$, R$^2$, R$^3$, R$^4$, R$^5$, R$^6$, R$^7$, R$^8$, R$^9$ and W$^3$ are each H; U is —OH, —COOH, —CONH$_2$, —CON(H)CH$_2$-furan-2-yl, —N(H)CH$_2$-furan-2-yl; A is a phenyl fused ring; Q is a phenyl group substituted by one or two substituents selected from chloro, trifluoromethyl and methoxy or Q is a 1,3-benzodioxolyl or a dihydrobenzofuranyl group; p is 1 or 2; n is 2; m is 1; q is 1; k is 0; t is 0; W$^1$ is unsubstituted phenyl; and W$^2$ is methyl or unsubstituted phenyl; or a pharmaceutically acceptable salt or solvate thereof.

19. A compound selected from:
2-[2-{[2-chloro-3-(trifluoromethyl)-benzyl](2,2-diphenylethyl)amino}ethyl]-5-benzofuran acetic acid,
2-[2-{[2,4-dimethoxy-benzyl](2,2-diphenylethyl)amino}ethyl]-5-benzofuran acetic acid,
2-[2-{[(2,3-methylenedioxy)benzyl](2,2-diphenylethyl)amino}ethyl]-5-benzofuran acetic acid,
2-[2-{[(2,3-dihydrobenzo[b]furan)methyl](2,2-diphenylethyl)amino}ethyl]-5-benzofuran acetic acid,
2-[2-{[4-methoxy-benzyl](2,2-diphenylethyl)amino}ethyl]-5-benzofuran acetic acid,
(R)-2-[2-{[2-chloro-3-(trifluoromethyl)-benzyl](2-methyl-2-phenylethyl)amino}ethyl]-5-benzofuran acetic acid,
(R)-2-[2-{[(2,3-dihydrobenzo[b]furan)methyl](2-methyl-2-phenylethyl)amino}ethyl]-5-benzofuran acetic acid,
(S)-2-[2-[{[2-chloro-3-(trifluoromethyl)-benzyl](2-methyl-2-phenylethyl)amino}ethyl]-benzofuran acetic acid,
(S)-2-[2-{[(2,3-dihydrobenzo[b]furan)methyl](2-methyl-2-phenylethyl)amino}ethyl]-5-benzofuran acetic acid,
2-{2-[[2-chloro-3-(trifluoromethyl)benzyl](2,2-diphenylethyl)amino]-ethyl}-6-benzofuran acetic acid,
2-[2-{[(2,3-methylenedioxy)benzyl](2,2-diphenylethyl)amino}ethyl]-6-benzofuran acetic acid,
2-[2-{[(2,4-dimethoxy)benzyl](2,2-diphenylethyl)amino}ethyl]-6-benzofuran acetic acid,
2-{2-[(4-methoxy-benzyl)(2,2-diphenylethyl)amino]-ethyl}-6-benzofuran acetic acid,
2-{2-[(2-chloro-3-(trifluoromethyl)-benzyl)-(2,2-diphenylethyl-amino]ethyl}-benzofuran-6-yl)-N-furan-2-yl methyl-acetamide,
2-{2-[(2,4-dimethoxy-benzyl)(2,2-diphenylethyl)-amino]ethyl}-benzofuran-6-yl)-N-furan-2-yl methyl-acetamide,
2-{2-[(2(chloro-3-(trifluoromethyl)-benzyl)(2,2-diphenylethyl-amino]ethyl}-benzofuran-6-yl)-acetamide,
2-{3-[(2-chloro-3-(trifluoromethyl)-benzyl)-(2-phenyl-propyl)-amino]-propyl}-benzofuran-6-yl)-acetic acid,
2-(2-{3-[(2-chloro-3-(trifluoromethyl)-benzyl-(2,2-diphenylethyl)-amino]-propyl}-benzofuran-6-yl)-ethanol,
2-(2-{3-[(2,4-dimethoxy)-benzyl-(2,2-diphenylethyl)-amino]-propyl}-benzofuran-6-yl)-ethanol, 2-{3-[(2-chloro-3-(trifluoromethyl)-benzyl)-((R)-2-phenyl-propyl)-amino]-propyl}-benzofuran-6-yl)-acetic acid,
2-{3-[(2-chloro-3-(trifluoromethyl)-benzyl)-((S)-2-phenyl-propyl)-amino]-propyl}-benzofuran-6-yl)-acetic acid,
(2-chloro-3-trifluoromethyl-benzyl)-(2,2-diphenyl-ethyl)-[3-(6-{2-[(furan-2-ylmethyl)-amino]-ethyl-benzofuran-2-yl)-propyl]-amine,
and a pharmaceutically acceptable salt or solvate thereof.

20. The compound according to claim 19, selected from:
2-[2-{[2,4-dimethoxy-benzyl](2,2-diphenylethyl)amino}ethyl]-5-benzofuran acetic acid,
(R)-2-[2-{[(2,3-dihydrobenzo[b]furan)methyl](2-methyl-2-phenylethyl)amino}ethyl]-5-benzofuran acetic acid,
2-{2-[[2-chloro-3-(trifluoromethyl)benzyl](2,2-diphenylethyl)amino]-ethyl}-6-benzofuran acetic acid,
2-[2-{[(2,4-dimethoxy)benzyl](2,2-diphenylethyl)amino}ethyl]-6-benzofuran acetic acid,
and a pharmaceutically acceptable salt or solvate thereof.

21. A pharmaceutical composition comprising a compound according to claim 1 and a pharmaceutically acceptable carrier or diluent.

22. A method for the prevention or treatment of an LXR mediated disease or condition comprising administering a therapeutically effective amount of a compound according to claim 1, wherein said LXR mediated disease or condition is atherosclerosis.

23. A method for the prevention or treatment of an LXR mediated disease or condition comprising administering a therapeutically effective amount of a compound according to claim 1, wherein said LXR mediated disease or condition is inflammation.

24. A method for increasing reverse cholesterol transport, said method comprising administering a therapeutically effective amount of a compound according to claim 1.

25. A method for inhibiting cholesterol absorption, said method comprising administering a therapeutically effective amount of a compound according to claim 1.

26. A compound selected from the group:
2-[2-[(2,2-diphenylethyl)amino]ethyl]-5-benzofuran acetic acid methyl ester,
2-[2-[[2-chloro-3-(trifluoromethyl)benzyl-(2,2-diphenylethyl)amino]ethyl]-5-benzofuran acetic acid methyl ester,
2-[2-{[2,4-dimethoxy-benzyl](2,2-diphenylethyl)amino}ethyl]-5-benzofuran acetic acid methyl ester,
2-[2-{[(2,3-methylenedioxy)benzyl](2,2-diphenylethyl)amino}ethyl]-5-benzofuran acetic acid methyl ester,
2-[2-{[(2,3-dihydrobenzo[b]furan)methyl] (2,2-diphenylethyl)amino}ethyl]-5-benzofuran acetic acid methyl ester,
2-[2-{[4-methoxy-benzyl](2,2-diphenylethyl)amino}ethyl]-5-benzofuran acetic acid methyl ester,
(R)-2-[2-[(2-methyl-2-phenylethyl)amino]ethyl]-5-benzofuran acetic acid methyl ester,
(R)-2-[2-{[2-chloro-3-(trifluoromethyl)-benzyl](2-methyl-2-phenylethyl)amino}ethyl]-5-benzofuran acetic acid methyl ester,
(R)-2-[2-{[(2,3-dihydrobenzo[b]furan)methyl](2-methyl-2-phenylethyl)amino}ethyl]-5-benzofuran acetic acid methyl ester,
(S)-2-[2-[(2-methyl-2-phenylethyl)amino]ethyl]-5-benzofuran acetic acid methyl ester, (S)-2-[2-[{[2-chloro-3-(trifluoromethyl)-benzyl](2-methyl-2-phenylethyl)amino}ethyl]-benzofuran acetic acid methyl ester,
(S)-2-[2-{[(2,3-dihydrobenzo[b]furan)methyl](2-methyl-2-phenylethyl)amino}ethyl]-5-benzofuran acetic acid methyl ester,
2-{2-[(2,2-diphenylethyl)amino]-ethyl}-6-benzofuran acetic acid methyl ester,
2-{2-[[2-chloro-3-(trifluoromethyl)benzyl](2,2-diphenylethyl)amino]-ethyl}-6-benzofuran acetic acid methyl ester,
2-[2-{[(2,3-methylenedioxy)benzyl](2,2-diphenylethyl)amino}ethyl]-6-benzofuran acetic acid methyl ester,
2-[2-{[(2,4-dimethoxy)benzyl](2,2-diphenylethyl)amino}ethyl]-6-benzofuran acetic acid methyl ester,
2-{2-[(4-methoxy-benzyl)(2,2-diphenylethyl)amino]-ethyl}-6-benzofuran acetic acid methyl ester, and a pharmaceutically acceptable salt or solvate thereof.

* * * * *